US012577403B2

(12) United States Patent
Matray et al.

(10) Patent No.: US 12,577,403 B2
(45) Date of Patent: Mar. 17, 2026

(54) ULTRA BRIGHT DIMERIC OR POLYMERIC DYES

(71) Applicant: SONY GROUP CORPORATION, Tokyo (JP)

(72) Inventors: Tracy Matray, Snohomish, WA (US); Sharat Singh, Los Altos Hills, CA (US); Michael VanBrunt, Bothell, WA (US)

(73) Assignee: SONY GROUP CORPORATION, Tokyo (JP)

( * ) Notice: Subject to any disclaimer, the term of this patent is extended or adjusted under 35 U.S.C. 154(b) by 0 days.

(21) Appl. No.: 18/632,909

(22) Filed: Apr. 11, 2024

(65) Prior Publication Data

US 2024/0287314 A1 Aug. 29, 2024

Related U.S. Application Data

(60) Continuation of application No. 17/458,938, filed on Aug. 27, 2021, now Pat. No. 11,981,820, which is a division of application No. 15/543,885, filed as application No. PCT/US2017/025530 on Mar. 31, 2017, now Pat. No. 11,142,647.

(60) Provisional application No. 62/317,192, filed on Apr. 1, 2016.

(51) Int. Cl.

| | |
|---|---|
| ***C09B 69/10*** | (2006.01) |
| ***C07C 215/68*** | (2006.01) |
| ***C07F 9/09*** | (2006.01) |
| ***C07F 9/24*** | (2006.01) |
| ***G01N 33/58*** | (2006.01) |

(52) U.S. Cl.

CPC .......... *C09B 69/102* (2013.01); *C07C 215/68* (2013.01); *C07F 9/091* (2013.01); *C07F 9/2408* (2013.01); *C09B 69/103* (2013.01); *C09B 69/109* (2013.01); *G01N 33/582* (2013.01)

(58) Field of Classification Search

CPC ... C09B 69/102; C09B 69/103; C09B 69/109; C07C 215/68; C07F 9/091; C07F 9/2408; G01N 33/582

USPC .......................................................... 558/169

See application file for complete search history.

(56) References Cited

U.S. PATENT DOCUMENTS

| | | | |
|---|---|---|---|
| 4,450,305 | A | 5/1984 | Kamhi |
| 4,476,229 | A | 10/1984 | Fino et al. |
| 4,778,753 | A | 10/1988 | Yamanishi et al. |
| 5,053,054 | A | 10/1991 | Kirchanski |
| 5,268,486 | A | 12/1993 | Waggoner et al. |
| 5,318,894 | A | 6/1994 | Pugia |
| 5,582,977 | A | 12/1996 | Yue et al. |
| 5,696,157 | A | 12/1997 | Wang et al. |
| 5,698,391 | A | 12/1997 | Cook et al. |
| 5,886,177 | A | 3/1999 | Cook et al. |
| 5,994,143 | A | 11/1999 | Bieniarz et al. |
| 6,005,093 | A | 12/1999 | Wood et al. |
| 6,140,480 | A | 10/2000 | Kool |
| 6,171,859 | B1 | 1/2001 | Herrnstadt et al. |
| 6,218,108 | B1 | 4/2001 | Kool |
| 6,365,730 | B1 | 4/2002 | Jennings et al. |
| 6,380,431 | B1 | 4/2002 | Whipple et al. |
| 6,479,650 | B1 | 11/2002 | Kool |
| 6,514,700 | B1 | 2/2003 | Singh |
| 6,534,041 | B1 | 3/2003 | Licha et al. |
| 6,627,400 | B1 | 9/2003 | Singh et al. |
| 6,670,193 | B2 | 12/2003 | Kool |
| 6,716,452 | B1 | 4/2004 | Piccariello et al. |
| 6,852,709 | B2 | 2/2005 | Leong et al. |
| 7,038,063 | B2 | 5/2006 | Lee et al. |
| 7,060,708 | B2 | 6/2006 | Piccariello et al. |
| 7,172,907 | B2 | 2/2007 | Chen et al. |
| 7,423,133 | B2 | 9/2008 | Kool et al. |
| 7,667,024 | B2 | 2/2010 | Mao et al. |
| 7,897,684 | B2 | 3/2011 | Bazan et al. |
| 8,008,522 | B2 | 8/2011 | Lukhtanov et al. |
| 8,101,776 | B2 | 1/2012 | Berens et al. |

(Continued)

FOREIGN PATENT DOCUMENTS

| | | | |
|---|---|---|---|
| CA | 2263671 | A1 | 2/1998 |
| CN | 102174078 | A | 9/2011 |

(Continued)

OTHER PUBLICATIONS

U.S. Appl. No. 18/898,324, filed Sep. 26, 2024.

(Continued)

*Primary Examiner* — Kristin A Vajda

(74) *Attorney, Agent, or Firm* — Seed Intellectual Property Law Group LLP

(57) ABSTRACT

Compounds useful as fluorescent or colored dyes are disclosed. The compounds have the following structure (II):

(II)

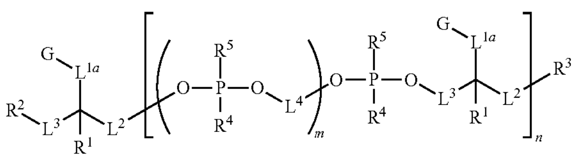

or a stereoisomer, tautomer or salt thereof, wherein $R^1$, $R^2$, $R^3$, $R^4$, $R^5$, $L^1$, $L^2$, $L^3$, $L^4$, M, m and n are as defined herein. Methods associated with preparation and use of such compounds are also provided.

8 Claims, 2 Drawing Sheets

(56) References Cited

U.S. PATENT DOCUMENTS

| | | | |
|---|---|---|---|
| 8,153,706 | B2 | 4/2012 | Vasudevan |
| 8,217,389 | B2 | 7/2012 | Nakano et al. |
| 8,293,700 | B2 | 10/2012 | Arranz |
| 8,349,308 | B2 | 1/2013 | Yurkovetskiy et al. |
| 8,354,515 | B2 | 1/2013 | Ueno et al. |
| 8,431,545 | B2 | 4/2013 | Kataoka et al. |
| 8,491,993 | B2 | 7/2013 | Nguyen et al. |
| 8,546,590 | B2 | 10/2013 | Gall |
| 8,632,947 | B2 | 1/2014 | Bentley et al. |
| 8,802,738 | B2 | 8/2014 | Emrick |
| 8,895,023 | B2 | 11/2014 | Rademacher et al. |
| 8,906,603 | B2 | 12/2014 | Castro et al. |
| 8,946,394 | B2 | 2/2015 | Na et al. |
| 9,029,537 | B2 | 5/2015 | Koch |
| 9,085,799 | B2 | 7/2015 | Bazan et al. |
| 9,150,782 | B2 | 10/2015 | Lee et al. |
| 9,400,273 | B1 | 7/2016 | Liu et al. |
| 9,545,447 | B2 | 1/2017 | Wooley et al. |
| 9,649,389 | B2 | 5/2017 | Groves et al. |
| 9,687,291 | B2 | 6/2017 | Shimizu et al. |
| 9,689,877 | B2 | 6/2017 | Matray et al. |
| 9,696,310 | B2 | 7/2017 | Margulies et al. |
| 9,714,946 | B2 | 7/2017 | Bradner et al. |
| 9,765,220 | B2 | 9/2017 | Matray et al. |
| 9,822,134 | B2 | 11/2017 | Segev |
| 9,851,359 | B2 | 12/2017 | Matray et al. |
| 9,884,070 | B2 | 2/2018 | Denardo et al. |
| 9,910,051 | B2 | 3/2018 | Beacham et al. |
| 9,913,992 | B2 | 3/2018 | Demarest et al. |
| 9,932,578 | B2 | 4/2018 | Feinstein et al. |
| 9,939,454 | B2 | 4/2018 | Dzubay et al. |
| 10,036,754 | B2 | 7/2018 | Matray et al. |
| 10,191,060 | B2 | 1/2019 | Chiu et al. |
| 10,435,563 | B2 | 10/2019 | Matray et al. |
| 10,617,670 | B2 | 4/2020 | Sapra et al. |
| 10,709,791 | B2 | 7/2020 | Stayton et al. |
| 10,834,091 | B2 | 11/2020 | Deninno et al. |
| 10,865,310 | B2 | 12/2020 | Matray et al. |
| 10,866,244 | B2 | 12/2020 | Matray et al. |
| 10,954,391 | B2 | 3/2021 | Matray et al. |
| 10,989,715 | B2 | 4/2021 | Matray et al. |
| 11,013,756 | B2 | 5/2021 | Haruta et al. |
| 11,084,932 | B2 | 8/2021 | Battrell et al. |
| 11,142,647 | B2 | 10/2021 | Matray et al. |
| 11,312,736 | B1 | 4/2022 | Matray et al. |
| 11,352,502 | B2 | 6/2022 | Matray et al. |
| 11,370,922 | B2 | 6/2022 | Matray et al. |
| 11,377,563 | B2 | 7/2022 | Matray et al. |
| 11,390,754 | B2 | 7/2022 | Singh et al. |
| 11,434,374 | B2 | 9/2022 | Matray et al. |
| 11,434,377 | B2 | 9/2022 | Matray et al. |
| 11,453,783 | B2 | 9/2022 | Matray et al. |
| 11,618,906 | B2 | 4/2023 | Steele et al. |
| 11,685,835 | B2 | 6/2023 | Matray |
| 11,827,661 | B2 | 11/2023 | Battrell et al. |
| 11,874,280 | B2 | 1/2024 | Jackson et al. |
| 11,931,419 | B2 | 3/2024 | Matray |
| 11,939,474 | B2 | 3/2024 | Matray et al. |
| 11,945,955 | B2 | 4/2024 | Matray |
| 11,981,820 | B2 | 5/2024 | Matray et al. |
| 12,006,438 | B2 | 6/2024 | Singh et al. |
| 12,018,159 | B2 | 6/2024 | Matray et al. |
| 12,076,407 | B2 | 9/2024 | Matray |
| 12,098,161 | B2 | 9/2024 | Matray et al. |
| 12,145,956 | B2 | 11/2024 | Matray et al. |
| 12,194,104 | B2 | 1/2025 | Matray |
| 2001/0018503 | A1 | 8/2001 | Whipple et al. |
| 2002/0012947 | A1 | 1/2002 | Bevers et al. |
| 2002/0099013 | A1 | 7/2002 | Piccariello et al. |
| 2002/0142329 | A1 | 10/2002 | Matray et al. |
| 2003/0054361 | A1 | 3/2003 | Heller |
| 2003/0207208 | A1 | 11/2003 | Uenishi |
| 2003/0207264 | A1 | 11/2003 | Packard et al. |
| 2004/0014981 | A1 | 1/2004 | Lugade et al. |
| 2004/0067498 | A1 | 4/2004 | Chenna et al. |
| 2004/0096825 | A1 | 5/2004 | Chenna et al. |
| 2004/0138467 | A1 | 7/2004 | French et al. |
| 2004/0224372 | A1 | 11/2004 | Li et al. |
| 2004/0241768 | A1 | 12/2004 | Whitten et al. |
| 2005/0054024 | A1 | 3/2005 | Lawrence |
| 2005/0123935 | A1 | 6/2005 | Haugland et al. |
| 2006/0008822 | A1 | 1/2006 | Manoharan et al. |
| 2006/0035302 | A1 | 2/2006 | Lee |
| 2006/0063186 | A1 | 3/2006 | Benson et al. |
| 2007/0042398 | A1 | 2/2007 | Peng et al. |
| 2007/0077549 | A1 | 4/2007 | Buller et al. |
| 2007/0148094 | A1 | 6/2007 | Uzgiris |
| 2007/0269902 | A1 | 11/2007 | Beechem et al. |
| 2008/0227939 | A1 | 9/2008 | Mizoshita et al. |
| 2009/0253792 | A1 | 10/2009 | Mickle et al. |
| 2009/0299070 | A1 | 12/2009 | Berens et al. |
| 2010/0021901 | A1 | 1/2010 | Yin et al. |
| 2010/0039684 | A1 | 2/2010 | Kolb et al. |
| 2010/0092386 | A1 | 4/2010 | Segev |
| 2010/0129800 | A1 | 5/2010 | Aymami Bofarull et al. |
| 2010/0192312 | A1 | 8/2010 | Cremer et al. |
| 2010/0248385 | A1 | 9/2010 | Tan et al. |
| 2011/0014599 | A1 | 1/2011 | Akhavan-Tafti et al. |
| 2011/0144065 | A1 | 6/2011 | Denardo et al. |
| 2011/0224516 | A1 | 9/2011 | Romey et al. |
| 2012/0021454 | A1 | 1/2012 | Bikker et al. |
| 2012/0116079 | A1 | 5/2012 | Lukhtanov et al. |
| 2012/0126175 | A1 | 5/2012 | Ueno et al. |
| 2013/0059343 | A1 | 3/2013 | Cheung |
| 2013/0119363 | A1 | 5/2013 | Sasaki et al. |
| 2013/0137755 | A1 | 5/2013 | Segev |
| 2013/0202536 | A1 | 8/2013 | Mustaev et al. |
| 2013/0244891 | A1 | 9/2013 | Waggoner et al. |
| 2014/0023590 | A1 | 1/2014 | Gao et al. |
| 2014/0193504 | A1 | 7/2014 | Wooley et al. |
| 2014/0275508 | A1 | 9/2014 | Scarr et al. |
| 2015/0030541 | A1 | 1/2015 | Rogers |
| 2015/0110715 | A1 | 4/2015 | Eder et al. |
| 2015/0159198 | A1 | 6/2015 | McGall et al. |
| 2015/0232615 | A1 | 8/2015 | Kwiatkowski |
| 2015/0258217 | A1 | 9/2015 | Caravan |
| 2016/0039850 | A1 | 2/2016 | Segev |
| 2016/0176903 | A1 | 6/2016 | Segev |
| 2016/0264737 | A1 | 9/2016 | Bartholomew et al. |
| 2016/0327859 | A1 | 11/2016 | Idei et al. |
| 2016/0347907 | A1 | 12/2016 | Dose |
| 2017/0292957 | A1 | 10/2017 | Matray et al. |
| 2017/0326233 | A1 | 11/2017 | Demeule et al. |
| 2018/0065998 | A1 | 3/2018 | Battrell et al. |
| 2018/0092993 | A1 | 4/2018 | Desai et al. |
| 2018/0141935 | A1 | 5/2018 | Josel et al. |
| 2018/0312468 | A1 | 11/2018 | Zhang et al. |
| 2019/0136065 | A1 | 5/2019 | Singh et al. |
| 2019/0144678 | A1 | 5/2019 | Matray et al. |
| 2019/0153232 | A1 | 5/2019 | Matray et al. |
| 2019/0177549 | A1 | 6/2019 | Matray et al. |
| 2019/0300716 | A1 | 10/2019 | Matray et al. |
| 2019/0378568 | A1 | 12/2019 | Robustelli |
| 2020/0032139 | A1 | 1/2020 | Behrendt et al. |
| 2020/0164085 | A1 | 5/2020 | Brandish et al. |
| 2020/0222554 | A1 | 7/2020 | Matray et al. |
| 2020/0330610 | A1 | 10/2020 | Desai et al. |
| 2020/0353089 | A1 | 11/2020 | Matray et al. |
| 2020/0353094 | A1 | 11/2020 | Matray et al. |
| 2020/0360526 | A1 | 11/2020 | Matray |
| 2021/0032277 | A1 | 2/2021 | Matray et al. |
| 2021/0032474 | A1 | 2/2021 | Matray et al. |
| 2021/0095130 | A1 | 4/2021 | Matray et al. |
| 2021/0096135 | A1 | 4/2021 | Matray et al. |
| 2021/0128591 | A1 | 5/2021 | Matray |
| 2021/0128739 | A1 | 5/2021 | Matray |
| 2021/0139440 | A1 | 5/2021 | Ramsden et al. |
| 2021/0253864 | A1 | 8/2021 | Matray et al. |
| 2021/0261782 | A1 | 8/2021 | Matray et al. |
| 2021/0285953 | A1 | 9/2021 | Matray et al. |
| 2021/0340380 | A1 | 11/2021 | Matray et al. |
| 2021/0395530 | A1 | 12/2021 | Matray et al. |
| 2022/0160887 | A1 | 5/2022 | Matray et al. |
| 2022/0168433 | A1 | 6/2022 | Matray et al. |

(56) References Cited

U.S. PATENT DOCUMENTS

| | | | |
|---|---|---|---|
| 2022/0168435 | A1 | 6/2022 | Matray et al. |
| 2022/0175951 | A1 | 6/2022 | Boitano et al. |
| 2022/0220314 | A1 | 7/2022 | Singh et al. |
| 2022/0227794 | A1 | 7/2022 | Matray et al. |
| 2022/0305127 | A1 | 9/2022 | Thomas et al. |
| 2022/0372297 | A1 | 11/2022 | Matray et al. |
| 2022/0380603 | A1 | 12/2022 | Matray et al. |
| 2022/0402963 | A1 | 12/2022 | Matray et al. |
| 2023/0012304 | A1 | 1/2023 | Matray et al. |
| 2023/0129481 | A1 | 4/2023 | Matray et al. |
| 2024/0043455 | A1 | 2/2024 | Battrell et al. |
| 2024/0092820 | A1 | 3/2024 | Matray et al. |
| 2024/0132725 | A1 | 4/2024 | Sherif |
| 2024/0207423 | A1 | 6/2024 | Matray |
| 2024/0210408 | A1 | 6/2024 | Jackson et al. |
| 2024/0248094 | A1 | 7/2024 | Matray et al. |
| 2024/0255514 | A1 | 8/2024 | Matray et al. |
| 2024/0287313 | A1 | 8/2024 | Sherif |
| 2024/0294767 | A1 | 9/2024 | Matray et al. |
| 2024/0318004 | A1 | 9/2024 | Singh et al. |
| 2024/0327440 | A1 | 10/2024 | Jackson et al. |
| 2024/0350645 | A1 | 10/2024 | Matray et al. |
| 2025/0009786 | A1 | 1/2025 | Matray et al. |
| 2025/0009898 | A1 | 1/2025 | Matray |

FOREIGN PATENT DOCUMENTS

| | | | | |
|---|---|---|---|---|
| CN | 103319378 | A | 9/2013 | |
| CN | 104072727 | A | 10/2014 | |
| CN | 105377994 | A | 3/2016 | |
| CN | 106589005 | A | 4/2017 | |
| CN | 107106685 | A | 8/2017 | |
| CN | 107454903 | A | 12/2017 | |
| CN | 107709470 | A | 2/2018 | |
| CN | 109153860 | A | 1/2019 | |
| EP | 0708837 | B1 | 5/1996 | |
| GB | 2 372 256 | A | 8/2002 | |
| GB | 2 554 666 | A | 4/2018 | |
| JP | S61207395 | A | 9/1986 | |
| JP | H04282391 | A | 10/1992 | |
| JP | 2000017183 | A | 1/2000 | |
| JP | 2003532092 | A | 10/2003 | |
| JP | 2011135823 | A | 7/2011 | |
| JP | 2014527071 | A | 10/2014 | |
| JP | 2016534107 | A | 11/2016 | |
| JP | 2017504659 | A | 2/2017 | |
| JP | 2017124994 | A | 7/2017 | |
| JP | 2018507863 | A | 3/2018 | |
| JP | 2018512167 | A | 5/2018 | |
| JP | 2018515628 | A | 6/2018 | |
| JP | 2019516807 | A | 6/2019 | |
| JP | 2019516821 | A | 6/2019 | |
| JP | 2021518410 | A | 8/2021 | |
| JP | 2021527911 | A | 10/2021 | |
| JP | 7069033 | B2 | 5/2022 | |
| JP | 7239904 | B2 | 3/2023 | |
| KR | 20030032939 | A | 4/2003 | |
| KR | 20100138910 | A | 12/2010 | |
| KR | 101041446 | B1 | 6/2011 | |
| KR | 10-2015-0007795 | A | 1/2015 | |
| KR | 20160022358 | A | 2/2016 | |
| KR | 20180005650 | A | 1/2018 | |
| KR | 10-2020-0133374 | A | 11/2020 | |
| KR | 20210032434 | A | 3/2021 | |
| KR | 102530707 | B1 | 5/2023 | |
| SU | 1121931 | A1 | 4/1988 | |
| WO | WO 9502700 | A1 | 1/1995 | |
| WO | WO 9506731 | A2 | 3/1995 | |
| WO | WO 9832463 | A2 | 7/1998 | |
| WO | WO 0173123 | A2 | 10/2001 | |
| WO | 0183502 | A1 | 11/2001 | |
| WO | WO 0222883 | A1 | 3/2002 | |
| WO | WO 02083954 | A1 | 10/2002 | |
| WO | WO 2004007751 | A2 | 1/2004 | |
| WO | WO 2007094135 | A1 | 8/2007 | |
| WO | WO 2009113645 | A1 | 9/2009 | |
| WO | WO 2010026957 | A1 | 3/2010 | |
| WO | WO 2011088193 | A2 | 7/2011 | |
| WO | WO 2013012687 | A2 | 1/2013 | |
| WO | WO 2014102803 | A1 | 7/2014 | |
| WO | WO 2014147642 | A1 | 9/2014 | |
| WO | WO-2015027176 | A1 * | 2/2015 | ............ C09B 11/24 |
| WO | WO 2015091953 | A1 | 6/2015 | |
| WO | WO 2015155753 | A2 | 10/2015 | |
| WO | 2016168750 | A1 | 10/2016 | |
| WO | WO 2016183185 | A1 | 11/2016 | |
| WO | WO 2017003639 | A2 | 1/2017 | |
| WO | WO 2017062271 | A2 | 4/2017 | |
| WO | WO 2017089890 | A1 | 6/2017 | |
| WO | WO 2017094897 | A1 | 6/2017 | |
| WO | WO 2017173355 | A1 | 10/2017 | |
| WO | WO 2017177065 | A2 | 10/2017 | |
| WO | WO 2017197144 | A1 | 11/2017 | |
| WO | WO 2018045278 | A1 | 3/2018 | |
| WO | WO 2019071208 | A1 | 4/2019 | |
| WO | WO 2019126691 | A1 | 6/2019 | |
| WO | WO 2019140227 | A1 | 7/2019 | |
| WO | WO 2019182765 | A1 | 9/2019 | |
| WO | WO 2019182766 | A1 | 9/2019 | |
| WO | 2020014634 | A1 | 1/2020 | |
| WO | WO 2020219959 | A1 | 10/2020 | |
| WO | 2021062176 | A2 | 4/2021 | |
| WO | 2022125564 | A1 | 6/2022 | |

OTHER PUBLICATIONS

U.S. Appl. No. 18/968,909, filed Dec. 4, 2024.
U.S. Appl. No. 19/030,635, filed Jan. 17, 2025.
U.S. Appl. No. 19/112,541, filed Mar. 17, 2025.
U.S. Appl. No. 19/112,548, filed Mar. 17, 2025.
U.S. Appl. No. 18/256,125, filed Jun. 6, 2023.
U.S. Appl. No. 18/412,316, filed Jan. 12, 2024.
U.S. Appl. No. 18/425,634, filed Jan. 29, 2024.
U.S. Appl. No. 18/436,594, filed Feb. 8, 2024.
U.S. Appl. No. 18/438,105, filed Feb. 9, 2024.
U.S. Appl. No. 18/570,283, filed Dec. 14, 2023.
U.S. Appl. No. 18/590,455, filed Feb. 28, 2024.
U.S. Appl. No. 18/290,630, filed Jan. 19, 2024.
U.S. Appl. No. 18/695,618, filed Mar. 26, 2024.
U.S. Appl. No. 18/695,674, filed Mar. 26, 2024.
U.S. Appl. No. 18/618,544, filed Mar. 27, 2024.
U.S. Appl. No. 18/678,656, filed Mar. 30, 2024.
"What is an Analyte?," Google Search, dated Mar. 22, 2018, retrieved from https://www.google.com/search?q=what+is+an+analyte&rlz=1C1GCEB_enUS775US775&oq=what+is+an+analyte&aqs=chrome..69i57j015.3231j0j7&s . . . 2 pages.
Arian et al., "1,9-Dialkoxyanthracene as a 1O2-Sensitive Linker," *J. Am. Chem. Soc.* 133:3972-3980, 2011.
Avirah et al., "Infrared Absorbing Croconaine Dyes: Synthesis and Metal Ion Binding Properties," *J. Org. Chem.* 73(1):274-279, 2008.
Aviñó et al., "Solid-phase synthesis of oligomers carrying several chromophore units linked by phosphodiester backbones," *Bioorganic & Medicinal Chemistry Letters* 18:2306-2310, 2008.
Babitskaya et al., "Bromoacyl Analogues of Phosphatidycholine with Intramolecular Fluorescence Quenching and Their Use as Substrates for Continuous Monitoring of Phospholipase A2 Activity," *Applied Biochemistry and Microbiology* 40(4):351-356, 2004.
Bag et al., "Triazolyl-donor-acceptor chromophore-decorated unnatural amino acids and peptides: FRET events in a β-turn conformation," *Chem. Commun.* 50:433-435, 2014.
Beaucage et al., "The Functionalization of Oligonucleotides Via Phosphoramidite Derivatives," *Tetrahedron* 49(10):1925-1963, 1993.
Becker et al., "New Thermotropic Dyes Based on Amino-Substituted Perylendicarboximides," *Chem. Eur. J.* 6(21):3984-3990, 2000.
Bergstrom et al., "A NaPi2b Antibody-Drug Conjugate Induces Durable Complete Tumor Regressions in Patient-Derived Xenograft Models of NSCLC," *IASLC 17th World Conference on Lung Cancer*, Vienna, Austria, Dec. 4-7, 2016 (8 pages).

(56) References Cited

OTHER PUBLICATIONS

Bergstrom et al., "A novel, highly potent HER2-targeted antibody-drug conjugate (ADC) for the treatment of low HER2-expressing tumors and combination with trastuzumab-based regimens in HER2-driven tumors," Mersana Therapeutics, Abstract LBA-231, 2015.

Bergstrom et al., "Potent Promise," *Innovations in Pharmaceutical Technology* 49:16-20, 2014.

Bergstrom et al., "XMT-1522 induces tumor regressions in pre-clinical models representing HER2-positive and HER2 low-expressing breast cancer," Mersana Therapeutics, Abstract P4-14-28, 2015, 1 page.

Boldyrev et al., "Synthesis and Characteristics of New Fluorescent Probes Based on Cardiolipin," *Russian Journal of Bioorganic Chemistry* 35(2):219-224, 2009.

Braeckmans et al., "Three-dimensional fluorescence recovery after photobleaching with the confocal scanning laser microscope," *Biophysical Journal* 85:2240-2252, 2003.

Braga et al., "Intracellular macromolecular mobility measured by fluorescence recovery after photobleaching with confocal laser scanning microscopes," *Molecular Biology of the Cell* 15:4749-4760, 2004.

Breul et al., "Fluorescent monomers as building blocks for dye labeled polymers: synthesis and application in energy conversion, biolabeling and sensors," Chem. Soc. Rev. 42(12):5366-5407, 2013.

Brinkley, "A brief survey of methods for preparing protein conjugates with dyes, haptens, and cross-linking reagents," *Bioconjugate Chem* 3:2-13, 1992.

Buckhout-White et al., "Assembling programmable FRET-based photonic networks using designer DNA scaffolds," *Nature Communications* 5:5615, Dec. 11, 2014. (16 pages).

CAPLUS Accession No. 1975: 171341, Holy, "Nucleic acid components and their analogs. CLXXII. Aliphatic analogs of nucleosides, nucleotides, and oligonucleotides," *Collection of Czechoslovak Chemical Communications* 40(1):187-214, 1975. (1 page).

CAPLUS Accession No. 1991:467753, Mielewczyk et al., "5' end fluorescent labelling of oligonucleotides with riboflavin-derived phosphitylating reagent," *Acta Biochimica Polonica* 36(3-4):225-233, 1989. (1 page).

CAPLUS Accession No. 1995:665426, Chen et al., "Synthesis of Novel Phosphoramidite Reagents for the Attachment of Antisense Oligonucleotides to Various Regions of the Benzophenanthridine Ring System," *Bioconjugate Chemistry* 6(4):473-482, Jul. 1, 1995. (1 page).

CAPLUS Accession No. 1995:733249, WO9506731A2, filed Mar. 9, 1995. (1 page).

CAPLUS Accession No. 1995:849926, Reed et al., "Structure-Activity Relationships of Cytotoxic Cholesterol-Modified DNA Duplexes," *Journal of Medicinal Chemistry* 38(22):4587-4596, Oct. 27, 1995. (1 page).

CAPLUS Accession No. 1997:497709, Puri et al., "Synthesis of 5'-polyarene-tethered oligo-DNAs and the thermal stability and spectroscopic properties of their duplexes and triplexes," *Tetrahedron* 53(30):10409-10432, Jul. 28, 1997. (1 page).

CAS Registry No. 862288-26-4, American Chemical Society, 2021. (1 page).

Chang et al., "A General Approach for Generating Fluorescent Probes to Visualize Piconewton Forces at the Cell Surface," *J. Am. Chem. Soc.* 138:2901-2904, 2016. (4 pages).

Chattopadhyay et al., "Brilliant Violet Fluorophores: A New Class of Ultrabright Fluorescent Compounds for Immunofluorescence Experiments," *Cytometry Part A* 81A:456-466, 2012.

Chen et al., "Synthesis and properties of new segmented block poly(urethane-urea)s containing phosphatidylcholine analogues and polybutadienes," *Macro-Molecular Chemistry and Physics* 197(5):1587-1597, May 1996. (11 pages).

Chen et al., "Synthesis of Novel Phosphoramidite Reagents for the Attachment of Antisense Oligonucleotides to Various Regions of the Benzophenanthridine Ring System," *Bioconjugate Chemistry* 6(4):473-482, Jul. 1, 1995. (10 pages).

Chong et al., "Oxygen Quenching of Pyrene-Lipid Fluorescence in Phosphatidylcholine Vesicles—A Probe for Membrane Organization," *Biophys. J.* 47:613-621, 1985.

Ciccotelli et al., "Polyguanine-conjugated antigens for scavenger receptor targeting and self-adjuvanting vaccines (VAC13P.1125)," *The Journal of Immunology* 194(Suppl. 1):214.5, May 1, 2015 [Abstract]. (1 page).

Cuppoletti et al., "Oligomeric fluorescent labels for DNA," *Bioconjug. Chem.* 16(3):528-534, 2005.

Dai et al., "DNA-polyfluorophore excimers as sensitive reporters for esterases and lipases," *Chem. Commun.* 46:1221-1223, 2010.

Damian et al., "Synthesis and DNA Interaction of Platinum Complex/Peptide Chimera as Potential Drug Candidates," *Eur. J. Org. Chem.* 6161-6170, 2010.

De Vos et al., "New Non Nucleosidic Phosphoramidites for the Solid Phase Multi-Labelling of Oligonucleotides: Comb- and Multifork-Like Structures," *Nucleosides & Nucleotides* 13(10):2245-2265, 1994.

Dioubankova et al., "Oligonucleotides containing new fluorescent 1-phenylethynylpyrene and 9,10-bis(phenylethynyl)anthracene uridine-2'-carbamates: synthesis and properties," *Tetrahedron* 60:4617-4626, 2004.

DiVittorio et al., "Synthetic peptides with selective affinity for apoptotic cells," *Org. Biomol. Chem.* 4:1966-1976, 2006.

Doi et al., "Hetero-Selective DNA-Like Duplex Stabilized by Donor-Acceptor Interactions," *Chem. Eur. J.* 21:15974-15980, 2015.

Drescher et al., "General Synthesis and Aggregation Behaviour of New Single-Chain Bolaphospholipids: Variations in Chain and Headgroup Structures," *Chemistry—A European Journal* 14(22):6796-6804, 2008.

Dropulic et al., "Update on New Antivirals Under Development for the Treatment of Double-Stranded DNA Virus Infections," Clinical Pharmacology & Therapeutics 88(5):610-619, Nov. 2010.

Dubrovsky, "Semiconductor nanoparticles as reporters in multiplexed immunoassay and cell analysis," *International Journal of Nanoscience* 8(1 & 2):163-167, 2009.

Finniss et al., "A versatile acid-labile linker for antibody-drug conjugates," Med. Chem, Commun; 5; Apr. 1, 2014, 4 pages.

Franceschin et al., "Synthesis of a Dibromoperylene Phosphoramidite Building Block and Its Incorporation at the 5' End of a G-Quadruplex Forming Oligonucleotide: Spectroscopic Properties and Structural Studies of the Resulting Dibromoperylene Conjugate," *Bioconjugate Chem* 22:1309-1319, 2011.

Franzini et al., "Identification of Structure-Activity Relationships from Screening a Structurally Compact DNA-Encoded Chemical Library," *Angewandte Chemie International Edition* 54:3927-3931, Feb. 3, 2015 [with supporting information]. (41 pages).

Gao et al., "Libraries of Composite Polyfluors Built from Fluorescent Deoxyribosides," *Journal of the American Chemical Society* 124:11590-11591, 2002.

Gao et al., "Modified DNA Analogues That Sense Light Exposure with Color Changes," *Journal of the American Chemical Society* 126:12748-12749, 2004.

Gordon et al., "Analysis of simulated and experimental fluorescence recovery after photobleaching. Data for two diffusing components," *Biophysical Journal* 68:766-778, 1995.

Griesang et al., "Four-Color, Enzyme-Free Interrogation of DNA Sequences with Chemically Activated, 3'-Fluorphore-Labeled Nucleotides," *Angew. Chem. Int. Ed.* 45:6144- 6148, 2006.

Gupta et al., "Dendrimers: Novel Polymeric Nanoarchitectures for Solubility Enhancement," *Biomacromolecules* 7(3):649-658, Mar. 2006 [Published online Feb. 15, 2006]. (10 pages).

Guryev et al., "Control of the Fluorescence of Dye-Antibody Conjugates by (2-Hydroxypropyl)-β-cyclodextrin in Fluorescence Microscopy and Flow Cytometry," *Analytical Chemistry* 83:7109-7114, Aug. 16, 2011.

Hanhela et al., "Synthesis and Evaluation of Fluorescent Materials for Colour Control of Peroxyoxalate Chemiluminescence. III. Yellow and Red Fluorescent Emitters," *Australian Journal of Chemistry* 34:1701-1717, 1981.

Haraguchi, "Live Cell Imaging: Approaches for Studying Protein Dynamics in Living Cells," *Cell Structure And Function* 27:333-334, 2002.

(56) References Cited

OTHER PUBLICATIONS

Hasegawa et al., "Cysteine, histidine and glycine exhibit anti-inflammatory effects in human coronary arterial endothelial cells," *Clinical and Experimental Immunology* 167:269-274, Jan. 11, 2012. (6 pages).
Irani et al., "Molecular properties of human IgG subclasses and their implications for designing therapeutic monoclonal antibodies against infectious diseases," *Molecular Immunology* 67:171-182, 2015.
Jain et al. "Current ADC Linker Chemistry," *Pharm. Res.* 32:3526-3540, 2015.
Johansson, "Choosing Reporter-Quencher Pairs for Efficient Quenching Through Formation of Intramolecular Dimers," *Methods in Molecular Biology* 335:17-29, 2006.
Kashida et al., "A Cationic Dye Triplet as a Unique "Glue" That Can Connect Fully Matched Termini of DNA Duplexes," *Chem. Eur. J.* 17:2614-2622, 2011.
Khandare et al., "Polymer-drug conjugates: Progress in polymeric prodrugs," *Progress in Polymer Science* 31(4):359-397, Apr. 2006. (39 pages).
Kolpashchikov, "Binary Probes for Nucleic Acid Analysis," *Chemical Reviews* 110(8):4709-4723, Jun. 28, 2010. (15 pages).
Koo et al., "Fluorescent DNA chemosensors: identification of bacterial species by their volatile metabolites," *Chemical Communications* 47:11435-11437, 2011.
Kozma et al., "Fluorescent Ligands for Adenosine Receptors," *Bioorganic & Medicinal Chemistry Letters* 23: 26-36, 2013.
Krueger at al., "Fluorescent Amino Acids: Modular Building Blocks for the Assembly of New Tools for Chemical Biology," *ChemBioChem* 14:788-799, 2013.
Lapeyre et al., "Aryldithioethyloxycarbonyl (Ardec): A New Family of Amine Protecting Groups Removable under Mild Reducing Conditions and Their Applications to Peptide Synthesis," *Chem. Eur. J.* 12:3655-3671, 2006.
Lee et al., "Monitoring the Hydrophobic Interactions of Internally Pyrene-Labeled Poly(ethylene oxide)s in Water by Fluorescence Spectroscopy," *Macromolecules* 31:9193-9200, 1998.
Leung et al., "7-Amino-4-Methyl-6-Sulfocoumarin-3-Acetic Acid: A Novel Blue Fluorescent Dye for Protein Labeling," *Bioorganic & Medicinal Chemistry Letters* 9: 2229- 2232, 1999.
Lewis et al., "Orientation Control of Fluorescence Resonance Energy Transfer Using DNA as a Helical Scaffold," *J. Am. Chem. Soc.* 127(28):10002-10003, 2005.
Li et al., "Polymeric Drugs: Advances in the development of pharmacologically active polymers," *Journal of Controlled Release* 219:369-382, 2015.
Li et al., "Responsive nanogel-based dual fluorescent sensors for temperature and Hg2+ ions with enhanced detection sensitivity," *J. Mater. Chem.* 20:10716-10723, 2010.
Liu et al., "Detection of prostate-specific membrane antigen on HUVECs in response to breast tumor-conditioned medium," *International Journal of Oncology* 38:1349-1355, 2011.
Liu et al., "DNA-Based Micelles: Synthesis, Micellar Properties and Size-Dependent Cell Permeability," *Chem. Eur. J.* 16:3791-3797, 2010 (14 Pages).
Liu et al., "Imidazole inhibits autophagy flux by blocking autophagic degradation and triggers apoptosis via increasing FoxO3a-Bim expression," *International Journal of Oncology* 46:721-731, Feb. 2015. (11 pages).
Liu et al., "Increased Cytotoxicity and Decreased In Vivo Toxicity of FdUMP[10] Relative to 5-FU," *Nucleosides & Nucleotides* 18(8):1789-1802, Aug. 1999. (14 pages).
Luo et al., "Sensitive and rapid quantification of C-reactive protein using quantum dot-labeled microplate immunoassay," *Journal of Translational Medicine* 10(24):1-9, 2012.
Malakhov et al., "1-(Phenylethynyl)pyrene and 9,10-Bis(phenylethynyl)anthracene, Useful Fluorescent Dyes for DNA Labeling: Excimer Formation and Energy Transfer," *Eur. J. Org. Chem:* 1298-1307, 2004.
Marras et al., "Efficiencies of fluorescence resonance energy transfer and contact-mediated quenching in oligonucleotide probes," *Nucleic Acids Research* 30(21):e122, Nov. 1, 2002. (8 pages).
Masuko et al., "Fluorescence resonance energy transfer from pyrene to perylene labels for nucleic acid hybridization assays under homogenous solution conditions," *Nucleic Acids Research* 28(8):e34, 2000 (8 pages).
McKinlay et al., "Cell-Penetrating, Guanidinium-Rich Oligophosphoesters: Effective and Versatile Molecular Transporters for Drug and Probe Delivery," *J. Am. Chem. Soc.* 138:3510-3517, Feb. 22, 2016.
Mersana Therapeutics, URL= http://www.mersana.com, download date Jan. 3, 2019, 9 pages.
Midoux et al., "Chemical vectors for gene delivery: a current review on polymers, peptides and lipids containing histidine or imidazole as nucleic acids carriers," *British Journal of Pharmacology* 157:166-178, May 2009. (13 pages).
Mielewczyk et al., "5' end fluorescent labelling of oligonucleotides with riboflavin-derived phosphitylating reagent," *Acta Biochimica Polonica* 36(3-4):225-233, 1989. (9 pages).
Molotkovsky et al., "Perylenoyl- and Anthrylvinyl-Labeled Lipids as Membrane Probes," *Biochimica et Biophysica Acta* 778:281-288, 1984.
Moss, "Nomenclature of Fused and Bridged Fused Ring Systems," *Pure & Appl. Chem.* 70(1):143-216, 1998.
Mthembu et al., "Breaking a Couple: Disulfide Reducing Agents," *ChemBioChem* 21, 2020. (10 pages).
Nolting, "Linker Technology for Antibody-Drug Conjugates," in Ducry (ed.), *Antibody-Drug Conjugates*, Humana Press, Totowa, NJ, 2013, Ch. 5, pp. 71-100.
Nussbaumer et al., "Amplification of Chirality by Supramolecular Polymerization of Pyrene Oligomers," *Angewandte Chemie International Edition* 50:5490-5494, 2011.
Oh et al., "Low-dose guanidine and pyridostigmine: relatively safe and effective long-term symptomatic therapy in Lambert-Eaton myasthenic syndrome," *Muscle & Nerve* 20:1146-1152, Sep. 1997. (7 pages).
Paris et al., "Probing DNA sequences in solution with a monomer-excimer fluorescence color change," *Nucleic Acids Research* 26(16):3789-3793, 1998.
Pelegrin et al., "Antiviral Monoclonal Antibodies: Can They Be More Than Simple Neutralizing Agents?" *Trends in Microbiology* 23(10):653-665, Oct. 2015.
Petersen et al., "Acyclic, achiral enamide nucleoside analogues. The importance of the C=C bond in the analogue for its ability to mimic natural nucleosides," *Organic & Biomolecular Chemistry* 1:3293-3296, Sep. 4, 2003. (4 pages).
Petreus et al., "Polyester imides containing main-chain phosphorus," *Revue Roumaine de Chimie* 34(8):971-978, 1994 (with English Abstract).
Phares et al., "Improving the Stability and Sensing of Electrochemical Biosensors by Employing Trithiol-Anchoring Groups in a Six-Carbon Self-Assembled Monolayer," *Anal. Chem.* 81(3):1095-1100, Feb. 1, 2009.
Poupart et al., "Aminopropargyl derivative of terpyridine-bis(methylenamine) tetraacetic acid chelate of europium (Eu (TMT)-AP3): a new reagent for fluorescent labelling of proteins and peptides," Org. Biomol. Chem. 4:4165-4177, Oct. 2006.
Pownall et al., "Kinetics of Spontaneous and Plasma-Stimulated Sphingomyelin Transfer," *Biochimica et Biophysica Acta* 712:169-176, 1982.
Pubchem, "U.S. Pat. No. 20100012929A1-20100121-C00010_4," SID No. 140452858, retrieved Mar. 29, 2016 from URL https://pubchem.ncbi.nlm.nih.gov/substance/140452858#sectio . . . , 6 pages.
Puri et al., "Synthesis of 5'-polyarene-tethered oligo-DNAs and the thermal stability and spectroscopic properties of their duplexes and triplexes," *Tetrahedron* 53(30):10409-10432, Jul. 28, 1997. (24 pages).
Reed et al., "Structure-Activity Relationships of Cytotoxic Cholesterol-Modified DNA Duplexes," *Journal of Medicinal Chemistry* 38(22):4587-4596, Oct. 27, 1995. (10 pages).

(56) References Cited

OTHER PUBLICATIONS

Ren et al., "An Antisense Oligodeoxynucleotide-Doxorubicin Conjugate: Preparation and Its Reversal Multidrug Resistance of Human Carcinoma Cell Line In Vitro," Nucleosides, Nucleotides & Nucleic Acids 23(10):1595-1607, 2004.
RN 230952-79-1, Registry Database Compound, 1999.
Rochat et al., "Water-Soluble Cationic Conjugated Polymers: Response to Electron-Rich Bioanalytes," *J. Am. Chem. Soc.* 135:17703-17706, 2013.
Rupcich et al., "Quenching of Fluorophore-Labeled DNA Oligonucleotides by Divalent Metal Ions: Implications for Selection, Design, and Applications of Signaling Aptamers and Signaling Deoxyribozymes," J. Am. Chem. Soc. 126(3):780-790, 2006.
Saito et al., "Dual-labeled oligonucleotide probe for sensing adenosine via FRET: A novel alternative to SNPs genotyping," Chem. Commun.:2133-2135, 2007.
Samal et al., "Cationic polymers and their therapeutic potential," *Chemical Society Reviews* 41:7147-7194, Aug. 2012. (48 pages).
Shuey et al., "Cyclohexanediol Bisphosphates as Models for Phospholipid-Metal Ion Binding Sites," *Bioorganic Chemistry* 21:95-108, Mar. 1993. (14 pages).
Shuman et al., "Bacterial DNA repair by non-homologous end joining," *Nature Reviews Microbiology* 5:852-861, Nov. 2007.
Singh et al., "Multiplexed measurement of membrane protein populations," *Caplus 2003*:769075, 2003. (2 pages).
Stewart et al., "The Fluorescence of a Chelating Two-Photon-Absorbing Dye is Enhanced with the Addition of Transition Metal Ions but Quenched in the Presence of Acid," *Proc. of SPIE* 9939:993904, 2016 (10 pages).
STIC Search Report from American Chemical Society, for U.S. Appl. No. 17/255,353, dated Sep. 7, 2023. (143 pages).
Striebel et al., "Enhancing sensitivity of human herpes virus diagnosis with DNA microarrays using dendrimers," *Experimental and Molecular Pathology* 77:89-97, Oct. 2004 [Published online Jul. 15, 2004]. (9 pages).
Stuart et al., "Site-Specific DNA-Doxorubicin Conjugates Display Enhanced Cytotoxicity to Breast Cancer Cells," *Bioconjugate Chemistry* 25:406-413, 2014.
Sun et al., "Dual-Color Fluorescence Imaging of Magnetic Nanoparticles in Live Cancer Cells Using Conjugated Polymer Probes," *Scientific Reports* 6:22368, 2016. (12 pages).
Sun et al., "High yield production of high molecular weight poly(ethylene glycol)/ α-cyclodextrin polyrotaxanes by aqueous one-pot approach," *Polymer* 53:2884-2889, 2012.
Sun et al., "Self-assembled biodegradable micellar nanoparticles of amphiphilic and cationic block copolymer for siRNA delivery," *Biomaterials* 29:4348-4355, available online Aug. 2008. (8 pages).
Sun et al., "Ultrabright and Multicolorful Fluorescence of Amphiphilic Polyethyleneimine Polymer Dots for Efficiently Combined Imaging and Therapy," *Scientific Reports* 3:3036, 2013. (6 pages).
Tabujew et al., "Chapter One: Functionalization of Cationic Polymers for Drug Delivery Applications," *RSC Polymer Chemistry Series* 13, 2015. (29 pages).
Takakusa et al., "Design and Synthesis of an Enzyme-Cleavable Sensor Molecule for Phosphodiesterase Activity Based on Fluorescence Resonance Energy Transfer," *J. Am. Chem. Soc.* 124(8):1653-1657, 2002.
Teo et al., "Polyfluorophores on a DNA Backbone: A Multicolor Set of Labels Excited at One Wavelength," *J. Am. Chem. Soc.* 131(11):3923-3933, 2009. (NIH Public Access Author Manuscript, available in PMC Mar. 25, 2010, 23 pages).
Teyssot et al., "Aromatic Nitrogen Donors for Efficient Copper(1)-NHC CuAAC under Reductant-Free Conditions," *Eur. J. Org. Chem.* 3507-3515, 2010.
Tram et al., "Oligonucleotide Labeling Using BODIPY Phosphoramidite," *Nucleosides, Nucleotides & Nucleic Acids* 30(1):1-11, 2011.
Vinogradov et al., "Total synthesis and biochemical characterization of mirror image barnase," *Chem Sci.* 6: 2997-3002, 2015.
Vybornyi et al., "Formation of Two-Dimensional Supramolecular Polymers by Amphiphilic Pyrene Oligomers," *Angew. Chem. Int. Ed.* 52:114488-11493, 2013.
Wang et al., "Cruciforms: Assembling Single Crystal Micro- and Nanostructures from One to Three Dimensions and Their Applications in Organic Field-Effect Transistors," *Chem. Mater.* 21:2840-2845, 2009.
Wang et al., "DNA Polyfluorophores for Real-Time Multicolor Tracking of Dynamic Biological Systems," *Angew. Chem. Int. Ed.* 51:7176-7180, 2012.
Wang et al., Fluorescence-Based Evaluation of the Partitioning of Lipids and Lipidated Peptides into Liquid-Ordered Lipid Microdomains: A Model for Molecular Partitioning into "Lipid Rafts," *Biophysical Journal* 79:919-933, Aug. 2000.
Wang et al., "Novel dexamethasone-HPMA copolymer conjugate and its potential application in treatment of rheumatoid arthritis," *Arthritis Research & Therapy* 9(1):R2, Jan. 18, 2007. (9 pages).
Wang, "Modern Synthetic Methods and Technologies of Polymers," Common Knowledge Evidence, Tongji University Press, 1st Edition, Jul. 2013, pp. 210-211. (includes portion of Chinese Office Action with English Summary of relevance) (20 pages).
Wilson et al., "Efficient Quenching of Oligomeric Fluorophores on a DNA Backbone," *Journal of the American Chemical Society* 129(50):15426-15427, 2007.
Wilson et al., "Oligodeoxyfluorosides: Strong Sequence of Dependence of Fluorescence Emission," *Tetrahedron* 63(17):3427-3433, 2007 (18 Pages).
Winiger et al., "Long-Distance Electronic Energy Transfer in Light-Harvesting Supramolecular Polymers," *Angew. Chem. Int. Ed.* 53:13609-13613, 2014.
Wu Yi et al., "$^{Py}$A-Modified Oligodeoxyadenylates: Expanded Fluorescence Phenomena and Structural Formation," *Chemistry—An Asian Journal* 7:60-63, Nov. 2011. (4 pages).
Yu et al., "Targeted Delivery of an Anti-Inflammatory PDE4 Inhibitor to Immune Cells via an Antibody-drug Conjugate," Molecular Therapy 24(12):2078-2089, Dec. 2016.
Yurkovetskiy et al., "Advantages of Polyacetal Polymer-based Antibody Drug Conjugates: Application to Low Expression Targets," Mersana Therapeutics, technical paper #2645, 2014, 1 page.
Zhang et al., "FRET Imaging of Enzyme-Responsive HPMA Copolymer Conjugate," *Macromol. Biosci.* 17:1600125, 2017 (8 pages).
Zhao et al., "Mussel-Inspired One-Pot Synthesis of a Fluorescent and Water-Soluble Polydopamine-Polyethyleneimine Copolymer," Macromol. Rapid Commun. 36:909-915, 2015.
Antos et al., "Site-Specific Protein Labeling via Sortase-Mediated Transpeptidation," Current Protocols in Protein Science, Chapter 15:15.3.1-15.3.9, Apr. 2009 (HHS Public Access Author Manuscript, available in PMC Aug. 1, 20170). (23 pages).
Doronina et al., "Development of potent monoclonal antibody auristatin conjugates for cancer therapy," Nature Biotechnology 21(7):778-784, Jul. 2003 [Published online Jun. 1, 2003] (with Erratum as published Nature Biotechnology 21(8):941, Aug. 2003). (8 pages).
Lee et al., "Targeted multimodal imaging modalities," Advanced Drug Delivery Reviews 76:60-78, Jul. 24, 2014. (19 pages).
Neidle et al. (Eds.), "Chapter 7: Acridine-based Anticancer Drugs," Molecular Aspects of Anticancer Drug-DNA Interactions, Topics in Molecule in Structural Biology, vol. 2, pp. 270-311, 1994. (52 pages).
Sousa et al., "Phenazines: Natural products for microbial growth control," hLife 2(3):100-112, Mar. 2024. (13 pages).
Wagenknecht, "Fluorescent DNA Base Modifications and Substitutes: Multiple Fluorophore Labeling and the DETEQ Concept," Annals of the New York Academy of Sciences 1130(1): 122-130, May 2008. (9 pages).
Bargh et al., "Cleavable linkers in antibody-drug conjugates," *Chemical Society Reviews* 48(16):4361-4374, Aug. 21, 2019. (15 pages).
Kozytska et al., "Discovery of the novel, homogenous payload platform Dolasynthen for Antibody-Drug Conjugates," Mersana Therapeutics, Abstract #272, 2018. (1 page).

(56) References Cited

OTHER PUBLICATIONS

Lee et al., "The spectroscopic analysis for binding of amphipathic and antimicrobial model peptides containing pyrenylalanine and tryptophan to lipid bilayer," *Biochimica et Biophysica Acta* 984:174-182, Sep. 4, 1989. (9 pages).
Liso et al., "Polymeric drugs derived from Ibuprofen with improved antiinflammatory profile," *Journal of Biomedical Materials Research* 32:553-560, Dec. 1996. (8 pages).
Lvnitski et al., "Introducing charge transfer functionality into prebiotically relevant β-sheet peptide fibrils," *Chemical Communications* 50:6733-6736, May 12, 2014. (4 pages).
Pawelczyk et al., "Molecular Consortia-Various Structural and Synthetic Concepts for More Effective Therapeutics Synthesis," *International Journal of Molecular Sciences* 19:1104, Apr. 6, 2018. (19 pages).
Xu et al., "Synthesis of [D-Pyrenylalanine4,4']gramicidin S by Solid-Phase-Synthesis and Cyclization-Cleavage Method with Oxime Resin," *Chemistry Letters* 21:191-194, Feb. 1992. (4 pages).

* cited by examiner

ULTRA BRIGHT DIMERIC OR POLYMERIC DYES

BACKGROUND

Technical Field

The present invention is generally directed to dimeric and polymeric fluorescent or colored dyes, and methods for their preparation and use in various analytical methods.

Description of the Related Art

Fluorescent and/or colored dyes are known to be particularly suitable for applications in which a highly sensitive detection reagent is desirable. Dyes that are able to preferentially label a specific ingredient or component in a sample enable the researcher to determine the presence, quantity and/or location of that specific ingredient or component. In addition, specific systems can be monitored with respect to their spatial and temporal distribution in diverse environments.

Fluorescence and colorimetric methods are extremely widespread in chemistry and biology. These methods give useful information on the presence, structure, distance, orientation, complexation and/or location for biomolecules. In addition, time-resolved methods are increasingly used in measurements of dynamics and kinetics. As a result, many strategies for fluorescence or color labeling of biomolecules, such as nucleic acids and protein, have been developed. Since analysis of biomolecules typically occurs in an aqueous environment, the focus has been on development and use of water soluble dyes.

Highly fluorescent or colored dyes are desirable since use of such dyes increases the signal to noise ratio and provides other related benefits. Accordingly, attempts have been made to increase the signal from known fluorescent and/or colored moieties. For example, dimeric and polymeric compounds comprising two or more fluorescent and/or colored moieties have been prepared in anticipation that such compounds would result in brighter dyes. However, as a result of intramolecular fluorescence quenching, the known dimeric and polymeric dyes have not achieved the desired increase in brightness.

There is thus a need in the art for water soluble dyes having an increased molar brightness. Ideally, such dyes and biomarkers should be intensely colored or fluorescent and should be available in a variety of colors and fluorescent wavelengths. The present invention fulfills this need and provides further related advantages.

BRIEF SUMMARY

In brief, embodiments of the present invention are generally directed to compounds useful as water soluble, fluorescent and/or colored dyes and/or probes that enable visual detection of analyte molecules, such as biomolecules, as well as reagents for their preparation. Methods for visually detecting analyte molecules using the dyes are also described.

The water soluble, fluorescent or colored dyes of embodiments of the invention are intensely colored and/or fluorescent and can be readily observed by visual inspection or other means. In some embodiments the compounds may be observed without prior illumination or chemical or enzymatic activation. By appropriate selection of the dye, as described herein, visually detectable analyte molecules of a variety of colors may be obtained.

In one embodiment, compounds having the following structure (I) are provided:

(I)

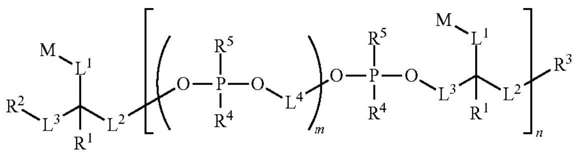

or a stereoisomer, tautomer or salt thereof, wherein $R^1$, $R^2$, $R^3$, $R^4$, $R^5$, $L^1$, $L^2$, $L^3$, $L^4$, M, m and n are as defined herein. Compounds of structure (I) find utility in a number of applications, including use as fluorescent and/or colored dyes in various analytical methods.

In another embodiment, a method for staining a sample is provided, the method comprises adding to said sample a compound of structure (I) in an amount sufficient to produce an optical response when said sample is illuminated at an appropriate wavelength.

In still other embodiments, the present disclosure provides a method for visually detecting an analyte molecule, comprising:

(a) providing a compound of (I); and (b) detecting the compound by its visible properties.

Other disclosed methods include a method for visually detecting a biomolecule, the method comprising:

(a) admixing a compound of structure (I) with one or more biomolecules; and (b) detecting the compound by its visible properties.

Other embodiments are directed to a composition comprising a compound of structure (I) and one or more biomolecules. Use of such compositions in analytical methods for detection of the one or more biomolecules is also provided.

In some other different embodiments is provided a compound of structure (II):

(II)

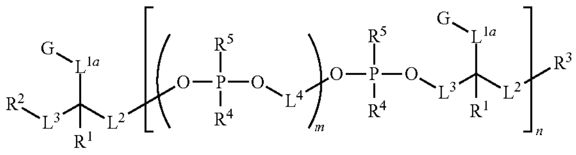

or a stereoisomer, salt or tautomer thereof, wherein $R^1$, $R^2$, $R^3$, $R^4$, $R^5$, $L^{1a}$, $L^2$, $L^3$, $L^4$, A, G, m and n are as defined herein. Compounds of structure (II) find utility in a number of applications, including use as intermediates for preparation of fluorescent and/or colored dyes of structure (I).

In yet other embodiments a method for labeling an analyte molecule is provided, the method comprising:

(a) admixing a compound of structure (II), wherein $R^2$ or $R^3$ is Q or a linker comprising a covalent bond to Q, with the analyte molecule;

(b) forming a conjugate of the compound and the analyte molecule; and (c) reacting the conjugate with a compound of formula $M\text{-}L^{1b}\text{-}G'$, thereby forming at least one covalent bond by reaction of G and G', wherein $R^2$, $R^3$, Q, G and $M\text{-}L^1b\text{-}G'$ are as defined herein.

In some different embodiments another method for labeling an analyte molecule is provided, the method comprising:

(a) admixing a compound of structure (II), wherein $R^2$ or $R^3$ is Q or a linker comprising a covalent bond to Q, with a compound of formula M-$L^{1b}$-G', thereby forming at least one covalent bond by reaction of G and G'; and (b) reacting the product of step (A) with the analyte molecule, thereby forming a conjugate of the product of step (A) and the analyte molecule wherein $R^2$, $R^3$, Q, G and M-$L^{1b}$-G' are as defined herein.

In more different embodiments, a method for preparing a compound of structure (I) is provided, the method comprising admixing a compound of structure (II) with a compound of formula M-$L^{1b}$-G', thereby forming at least one covalent bond by reaction of G and G', wherein G and M-$L^{1b}$-G' are as defined herein.

These and other aspects of the invention will be apparent upon reference to the following detailed description.

BRIEF DESCRIPTION OF THE SEVERAL VIEWS OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

Figure 1:
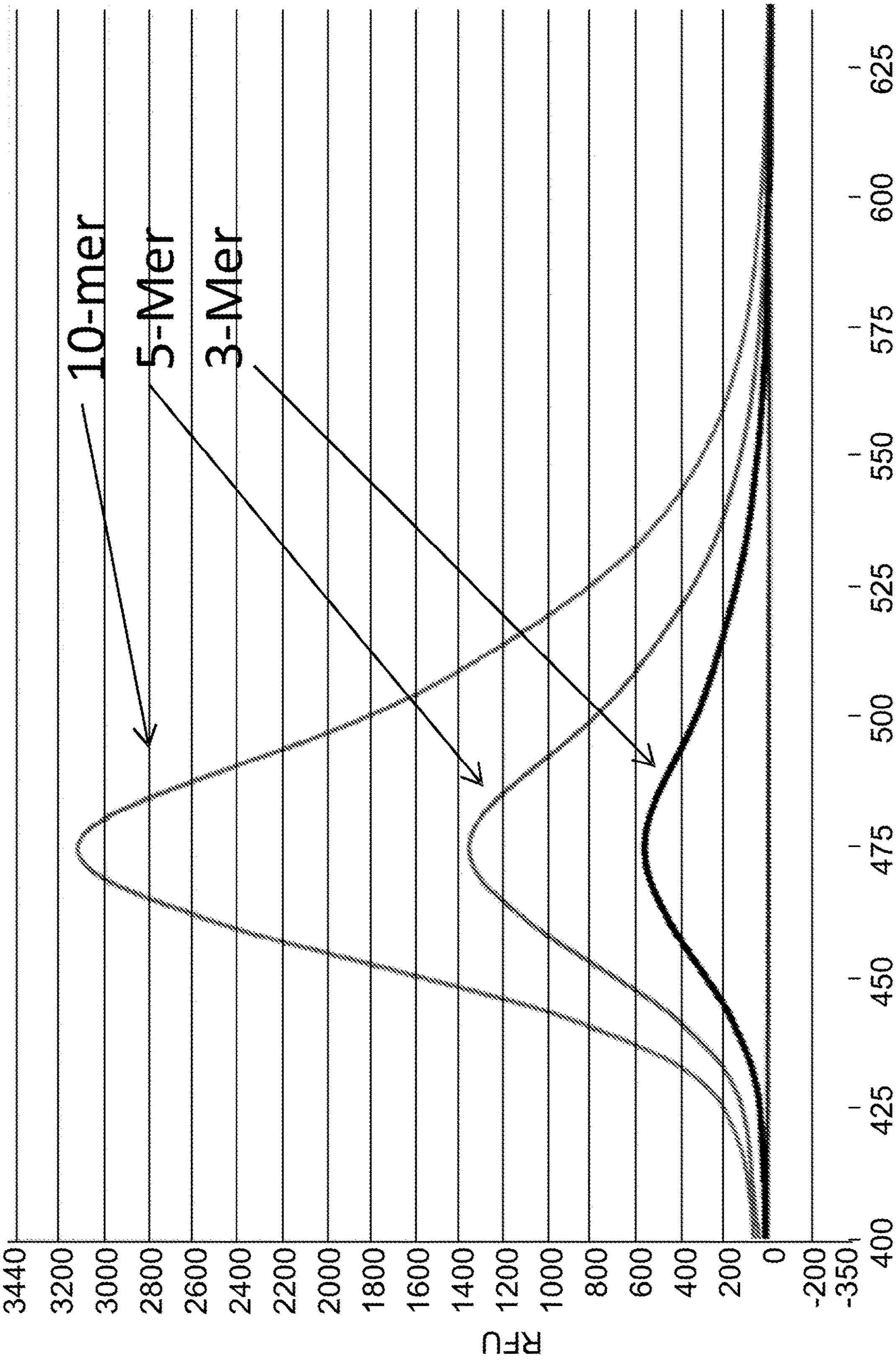
FIG. 1 provides fluorescence spectra for 3-mer, 5-mer and 10-mer coumarin dye compounds.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the $-NH_2$ group.

"Carboxy" refers to the $-CO_2H$ group.

"Cyano" refers to the —CN group.

"Formyl" refers to the —C(=O)H group.

"Hydroxy" or "hydroxyl" refers to the —OH group.

"Imino" refers to the =NH group.

"Nitro" refers to the $-NO_2$ group.

"Oxo" refers to the =O substituent group.

"Sulfhydryl" refers to the —SH group.

"Thioxo" refers to the =S group.

"Alkyl" refers to a straight or branched hydrocarbon chain group consisting solely of carbon and hydrogen atoms, containing no unsaturation, having from one to twelve carbon atoms ($C_1$-$C_{12}$ alkyl), one to eight carbon atoms ($C_1$-$C_5$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, alkyl groups are optionally substituted.

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, alkylene is optionally substituted.

"Alkenylene" or "alkenylene chain" refers to a straight or branched divalent hydrocarbon chain linking the rest of the molecule to a radical group, consisting solely of carbon and hydrogen, containing at least one carbon-carbon double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, alkenylene is optionally substituted.

"Alkynylene" or "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms, e.g., ethenylene, propenylene, n-butenylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, alkynylene is optionally substituted.

"Alkylether" refers to any alkyl group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylethers include at least one carbon oxygen bond, but may include more than one. For example, polyethylene glycol (PEG) is included within the meaning of alkylether. Unless stated otherwise specifically in the specification, an alkylether group is optionally substituted. For example, in some embodiments an alkylether is substituted with an alcohol or —OP(=$R_a$)($R_b$)$R_c$, wherein each of $R_a$, $R_b$ and $R_c$ is as defined for compounds of structure (I).

"Alkoxy" refers to a group of the formula —$OR_a$ where $R_a$ is an alkyl group as defined above containing one to twelve carbon atoms. Unless stated otherwise specifically in the specification, an alkoxy group is optionally substituted.

"Heteroalkylene" refers to an alkylene group, as defined above, comprising at least one heteroatom (e.g., N, O, P or S) within the alkylene chain or at a terminus of the alkylene chain. In some embodiments, the heteroatom is within the alkylene chain (i.e., the heteroalkylene comprises at least one carbon-heteroatom-carbon bond). In other embodiments, the heteroatom is at a terminus of the alkylene and thus serves to join the alkylene to the remainder of the molecule (e.g., M1-H-A-M2, where M1 and M2 are portions of the molecule, H is a heteroatom and A is an alkylene). Unless stated otherwise specifically in the specification, a heteroalkylene group is optionally substituted. An exemplary heteroalkylene linking group is illustrated below:

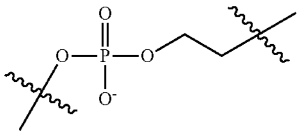

"C linker"

Multimers of the above C-linker are included in various embodiments of heteroalkylene linkers.

"Heteroalkenylene" is a heteroalkylene, as defined above, comprising at least one carbon-carbon double bond. Unless stated otherwise specifically in the specification, a heteroalkenylene group is optionally substituted.

"Heteroalkynylene" is a heteroalkylene comprising at least one carbon-carbon triple bond. Unless stated otherwise specifically in the specification, a heteroalkynylene group is optionally substituted.

"Heteroatomic" in reference to a "heteroatomic linker" refers to a linker group consisting of one or more heteroatom. Exemplary heteroatomic linkers include single atoms selected from the group consisting of O, N, P and S, and multiple heteroatoms for example a linker having the formula —P($O^-$)(=O)O— or —OP($O^-$)(=O)O— and multimers and combinations thereof.

"Phosphate" refers to the —OP(=O)($R_a$)Re group, wherein $R_a$ is OH, $O^-$ or $OR_c$; and Re is OH, $O^-$, $OR_c$, a thiophosphate group or a further phosphate group, wherein $R_c$ is a counter ion (e.g., Na+ and the like).

"Phosphoalkyl" refers to the —OP(=O)($R_a$)$R_b$ group, wherein $R_a$ is OH, $O^-$ or $OR_c$; and $R_b$ is —Oalkyl, wherein $R_c$ is a counter ion (e.g., Na+ and the like). Unless stated otherwise specifically in the specification, a phosphoalkyl group is optionally substituted. For example, in certain embodiments, the —Oalkyl moiety in a phosphoalkyl group is optionally substituted with one or more of hydroxyl, amino, sulfhydryl, phosphate, thiophosphate, phosphoalkyl, thiophosphoalkyl, phosphoalkylether or thiophosphoalkylether.

"Phosphoalkylether" refers to the —OP(=O)($R_a$)$R_b$ group, wherein $R_a$ is OH, $O^-$ or $OR_c$; and $R_b$ is —Oalkylether, wherein $R_c$ is a counter ion (e.g., Na+ and the like). Unless stated otherwise specifically in the specification, a phosphoalkylether group is optionally substituted. For example, in certain embodiments, the —Oalkylether moiety in a phosphoalkylether group is optionally substituted with one or more of hydroxyl, amino, sulfhydryl, phosphate, thiophosphate, phosphoalkyl, thiophosphoalkyl, phosphoalkylether or thiophosphoalkylether.

"Thiophosphate" refers to the —OP(=$R_a$)($R_b$)$R_c$ group, wherein $R_a$ is O or S, Re is OH, O–, S–, $OR_d$ or $SR_d$; and $R_c$ is OH, SH, $O^-$, $S^-$, $OR_d$, $SR_d$, a phosphate group or a further thiophosphate group, wherein $R_d$ is a counter ion (e.g., Na+ and the like) and provided that: i) $R_a$ is S; ii) $R_b$ is $S^-$ or $SR_d$; iii) $R_c$ is SH, $S^-$ or $SR_d$; or iv) a combination of i), ii) and/or iii).

"Thiophosphoalkyl" refers to the —OP(=$R_a$)($R_b$)$R_c$ group, wherein $R_a$ is O or S, Re is OH, $O^-$, $S^-$, $OR_d$ or $SR_d$; and $R_c$ is —Oalkyl, wherein $R_d$ is a counter ion (e.g., Na+ and the like) and provided that: i) $R_a$ is S; ii) $R_b$ is $S^-$ or $SR_d$; or iii)$R_a$ is S and $R_b$ is $S^-$ or $SR_d$. Unless stated otherwise specifically in the specification, a thiophosphoalkyl group is optionally substituted. For example, in certain embodiments, the —Oalkyl moiety in a thiophosphoalkyl group is optionally substituted with one or more of hydroxyl, amino, sulfhydryl, phosphate, thiophosphate, phosphoalkyl, thiophosphoalkyl, phosphoalkylether or thiophosphoalkylether.

"Thiophosphoalkylether" refers to the —OP(=$R_a$)($R_b$)$R_c$ group, wherein $R_a$ is O or S, Re is OH, $O^-$, $S^-$, $OR_d$ or $SR_d$; and $R_c$ is —Oalkylether, wherein $R_d$ is a counter ion (e.g., Na+ and the like) and provided that: i) $R_a$ is S; ii) $R_b$ is $S^-$ or $SR_d$; or iii)$R_a$ is S and $R_b$ is $S^-$ or $SR_d$. Unless stated otherwise specifically in the specification, a thiophosphoalkylether group is optionally substituted. For example, in certain embodiments, the —Oalkylether moiety in a thiophosphoalkyl group is optionally substituted with one or more of hydroxyl, amino, sulfhydryl, phosphate, thiophosphate, phosphoalkyl, thiophosphoalkyl, phosphoalkylether or thiophosphoalkylether.

"Carbocyclic" refers to a stable 3- to 18-membered aromatic or non-aromatic ring comprising 3 to 18 carbon atoms. Unless stated otherwise specifically in the specification, a carbocyclic ring may be a monocyclic, bicyclic, tricyclic or tetracyclic ring system, which may include fused or bridged ring systems, and may be partially or fully saturated. Non-aromatic carbocyclyl radicals include cycloalkyl, while aromatic carbocyclyl radicals include aryl. Unless stated otherwise specifically in the specification, a carbocyclic group is optionally substituted.

"Cycloalkyl" refers to a stable non-aromatic monocyclic or polycyclic carbocyclic ring, which may include fused or bridged ring systems, having from three to fifteen carbon atoms, preferably having from three to ten carbon atoms, and which is saturated or unsaturated and attached to the rest of the molecule by a single bond. Monocyclic cyclocalkyls include, for example, cyclopropyl, cyclobutyl, cyclopentyl, cyclohexyl, cycloheptly, and cyclooctyl. Polycyclic cycloalkyls include, for example, adamantyl, norbornyl, decalinyl, 7,7-dimethyl-bicyclo-[2.2.1]heptanyl, and the like. Unless stated otherwise specifically in the specification, a cycloalkyl group is optionally substituted.

"Aryl" refers to a ring system comprising at least one carbocyclic aromatic ring. In some embodiments, an aryl crromprises from 6 to 18 carbon atoms. The aryl ring may be a monocyclic, bicyclic, tricyclic or tetracyclic ring system, which may include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted.

"Heterocyclic" refers to a stable 3- to 18-membered aromatic or non-aromatic ring comprising one to twelve carbon atoms and from one to six heteroatoms selected from the group consisting of nitrogen, oxygen and sulfur. Unless stated otherwise specifically in the specification, the heterocyclic ring may be a monocyclic, bicyclic, tricyclic or tetracyclic ring system, which may include fused or bridged ring systems; and the nitrogen, carbon or sulfur atoms in the heterocyclic ring may be optionally oxidized; the nitrogen atom may be optionally quaternized; and the heterocyclic ring may be partially or fully saturated. Examples of aromatic heterocyclic rings are listed below in the definition of heteroaryls (i.e., heteroaryl being a subset of heterocyclic). Examples of non-aromatic heterocyclic rings include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, pyrazolopyrimidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclic group is optionally substituted.

"Heteroaryl" refers to a 5- to 14-membered ring system comprising one to thirteen carbon atoms, one to six heteroatoms selected from the group consisting of nitrogen, oxygen and sulfur, and at least one aromatic ring. For purposes of certain embodiments of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e., thienyl). Unless stated otherwise specifically in the specification, a heteroaryl group is optionally substituted.

"Fused" refers to a ring system comprising at least two rings, wherein the two rings share at least one common ring atom, for example two common ring atoms. When the fused ring is a heterocyclyl ring or a heteroaryl ring, the common ring atom(s) may be carbon or nitrogen. Fused rings include bicyclic, tricyclic, tertracyclic, and the like.

The term "substituted" used herein means any of the above groups (e.g., alkyl, alkylene, alkenylene, alkynylene, heteroalkylene, heteroalkenylene, heteroalkynylene, alkoxy, alkylether, phosphoalkyl, phosphoalkylether, thiophosphoalkyl, thiophosphoalkylether, carbocyclic, cycloalkyl, aryl, heterocyclic and/or heteroaryl) wherein at least one hydrogen atom (e.g., 1, 2, 3 or all hydrogen atoms) is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Conjugation" refers to the overlap of one p-orbital with another p-orbital across an intervening sigma bond. Conjugation may occur in cyclic or acyclic compounds. A "degree of conjugation" refers to the overlap of at least one p-orbital with another p-orbital across an intervening sigma bond. For example, 1, 3-butadine has one degree of conjugation, while benzene and other aromatic compounds typically have multiple degrees of conjugation. Fluorescent and colored compounds typically comprise at least one degree of conjugation.

"Fluorescent" refers to a molecule which is capable of absorbing light of a particular frequency and emitting light of a different frequency. Fluorescence is well-known to those of ordinary skill in the art.

"Colored" refers to a molecule which absorbs light within the colored spectrum (i.e., red, yellow, blue and the like).

A "linker" refers to a contiguous chain of at least one atom, such as carbon, oxygen, nitrogen, sulfur, phosphorous and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions.

The term "biomolecule" refers to any of a variety of biological materials, including nucleic acids, carbohydrates, amino acids, polypeptides, glycoproteins, hormones, aptamers and mixtures thereof. More specifically, the term is intended to include, without limitation, RNA, DNA, oligonucleotides, modified or derivatized nucleotides, enzymes, receptors, prions, receptor ligands (including hormones), antibodies, antigens, and toxins, as well as bacteria, viruses, blood cells, and tissue cells. The visually detectable biomolecules of the invention (e.g., compounds of structure (I) having a biomolecule linked thereto) are prepared, as further described herein, by contacting a biomolecule with a compound having a reactive group that enables attachment of the biomolecule to the compound via any available atom or functional group, such as an amino, hydroxy, carboxyl, or sulfhydryl group on the biomolecule.

A "reactive group" is a moiety capable of reacting with a second reactive groups (e.g., a "complementary reactive group") to form one or more covalent bonds, for example by a displacement, oxidation, reduction, addition or cycloaddition reaction. Exemplary reactive groups are provided in Table 1, and include for example, nucleophiles, electrophiles, dienes, dienophiles, aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, $\alpha,\beta$-unsaturated carbonyl, alkene, maleimide, $\alpha$-haloimide, epoxide, aziridine, tetrazine, tetrazole, phosphine, biotin, thiirane and the like.

The terms "visible" and "visually detectable" are used herein to refer to substances that are observable by visual inspection, without prior illumination, or chemical or enzymatic activation. Such visually detectable substances absorb and emit light in a region of the spectrum ranging from about 300 to about 900 nm. Preferably, such substances are intensely colored, preferably having a molar extinction coefficient of at least about 40,000, more preferably at least about 50,000, still more preferably at least about 60,000, yet still more preferably at least about 70,000, and most preferably at least about 80,000 $M^{-1}cm^{-1}$. The compounds of the invention may be detected by observation with the naked eye, or with the aid of an optically based detection device, including, without limitation, absorption spectrophotometers, transmission light microscopes, digital cameras and scanners. Visually detectable substances are not limited to those which emit and/or absorb light in the visible spectrum. Substances which emit and/or absorb light in the ultraviolet (UV) region (about 10 nm to about 400 nm), infrared (IR) region (about 700 nm to about 1 mm), and substances emitting and/or absorbing in other regions of the electromagnetic spectrum are also included with the scope of "visually detectable" substances.

For purposes of embodiments of the invention, the term "photostable visible dye" refers to a chemical moiety that is visually detectable, as defined hereinabove, and is not significantly altered or decomposed upon exposure to light. Preferably, the photostable visible dye does not exhibit significant bleaching or decomposition after being exposed to light for at least one hour. More preferably, the visible dye is stable after exposure to light for at least 12 hours, still more preferably at least 24 hours, still yet more preferably at least one week, and most preferably at least one month. Nonlimiting examples of photostable visible dyes suitable for use in the compounds and methods of the invention include azo dyes, thioindigo dyes, quinacridone pigments, dioxazine, phthalocyanine, perinone, diketopyrrolopyrrole, quinophthalone, and truarycarbonium.

As used herein, the term "perylene derivative" is intended to include any substituted perylene that is visually detectable. However, the term is not intended to include perylene itself. The terms "anthracene derivative", "naphthalene derivative", and "pyrene derivative" are used analogously. In some preferred embodiments, a derivative (e.g., perylene, pyrene, anthracene or naphthalene derivative) is an imide, bisimide or hydrazamimide derivative of perylene, anthracene, naphthalene, or pyrene.

The visually detectable molecules of various embodiments of the invention are useful for a wide variety of analytical applications, such as biochemical and biomedical applications, in which there is a need to determine the presence, location, or quantity of a particular analyte (e.g., biomolecule). In another aspect, therefore, the invention provides a method for visually detecting a biomolecule, comprising: (a) providing a biological system with a visually detectable biomolecule comprising the compound of structure (I) linked to a biomolecule; and (b) detecting the biomolecule by its visible properties. For purposes of the invention, the phrase "detecting the biomolecule by its visible properties" means that the biomolecule, without illumination or chemical or enzymatic activation, is observed with the naked eye, or with the aid of a optically based detection device, including, without limitation, absorption spectrophotometers, transmission light microscopes, digital cameras and scanners. A densitometer may be used to quantify the amount of visually detectable biomolecule present. For example, the relative quantity of the biomolecule in two samples can be determined by measuring relative optical density. If the stoichiometry of dye molecules per biomolecule is known, and the extinction coefficient of the dye molecule is known, then the absolute concentration of the biomolecule can also be determined from a measurement of optical density. As used herein, the term "biological system" is used to refer to any solution or mixture comprising one or more biomolecules in addition to the visually detectable biomolecule. Nonlimiting examples of such biological systems include cells, cell extracts, tissue samples, electrophoretic gels, assay mixtures, and hybridization reaction mixtures.

"Solid support" refers to any solid substrate known in the art for solid-phase support of molecules, for example a "microparticle" refers to any of a number of small particles useful for attachment to compounds of the invention, including, but not limited to, glass beads, magnetic beads, polymeric beads, nonpolymeric beads, and the like. In certain embodiments, a microparticle comprises polystyrene beads.

"Base pairing moiety" refers to a heterocyclic moiety capable of hybridizing with a complementary heterocyclic moiety via hydrogen bonds (e.g., Watson-Crick base pairing). Base pairing moieties include natural and unnatural bases. Non-limiting examples of base pairing moieties are RNA and DNA bases such adenosine, guanosine, thymidine, cytosine and uridine and analogues thereof.

Embodiments of the invention disclosed herein are also meant to encompass all compounds of structure (I) or (II) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, 35S, $^{18}F$, $^{36}Cl$, $^{123}I$, and $^{125}J$, respectively.

Isotopically-labeled compounds of structure (I) (II) can generally be prepared by conventional techniques known to those skilled in the art or by processes analogous to those described below and in the following Examples using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution.

"Salt" includes both acid and base addition salts.

"Acid addition salt" refers to those salts which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Base addition salt" refers to those salts which are prepared from addition of an inorganic base or an organic base to the free acid. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Crystallizations may produce a solvate of the compounds described herein. Embodiments of the present invention include all solvates of the described compounds. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compounds of the invention may be true solvates, while in other cases the compounds of the invention may merely retain adventitious water or another solvent or be a mixture of water plus some adventitious solvent.

Embodiments of the compounds of the invention (e.g., compounds of structure I or II), or their salts, tautomers or solvates may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. Embodiments of the present invention are meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds. Various tautomeric forms of the compounds are easily derivable by those of ordinary skill in the art.

The chemical naming protocol and structure diagrams used herein are a modified form of the I.U.P.A.C. nomenclature system, using the ACD/Name Version 9.07 software program and/or ChemDraw Ultra Version 11.0 software naming program (CambridgeSoft). Common names familiar to one of ordinary skill in the art are also used.

As noted above, in one embodiment of the present invention, compounds useful as fluorescent and/or colored dyes in various analytical methods are provided. In other embodiments, compounds useful as synthetic intermediates for preparation of compounds useful as fluorescent and/or colored dyes are provided. In general terms, embodiments of the present invention are directed to dimers and higher polymers of fluorescent and/or colored moieties. The fluorescent and or colored moieties are linked by a phosphorous-containing linkage. Without wishing to be bound by theory, it is believed the linker helps to maintain sufficient spatial distance between the fluorescent and/or colored moieties such that intramolecular quenching is reduced or eliminated, thus resulting in a dye compound having a high molar "brightness" (e.g., high fluorescence emission).

Accordingly, in some embodiments the compounds have the following structure (A):

(A)

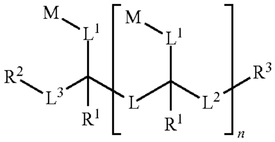

wherein L is a phosphorous-containing linkage sufficient to maintain spatial separation between one or more (e.g., each) M group so that intramolecular quenching is reduced or eliminated, and $R^1$, $R^2$, $R^3$, $L^1$, $L^2$, $L^3$ and n are as defined for structure (I).

In other embodiments is provided a compound having the following structure (I):

(I)

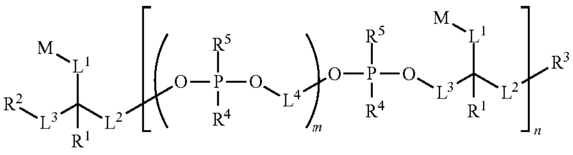

or a stereoisomer, salt or tautomer thereof, wherein:

M is, at each occurrence, independently a moiety comprising two or more carbon-carbon double bonds and at least one degree of conjugation;

$L^1$ is, at each occurrence, independently a linker comprising a functional group capable of formation by reaction of two complementary reactive groups;

$L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently an alkylene, alkenylene, alkynylene, heteroalkylene, heteroalkenylene or heteroalkynylene linker;

$R^1$ is, at each occurrence, independently H, alkyl or alkoxy;

$R^2$ and $R^3$ are each independently H, OH, SH, alkyl, alkoxy, alkylether, —OP(═$R_a$)($R_b$)$R_c$, Q, a linker comprising a covalent bond to Q, a linker comprising a covalent bond to an analyte molecule, a linker comprising a covalent bond to a solid support or a linker comprising a covalent bond to a further compound of structure (I), wherein: $R_a$ is O or S; $R_b$ is OH, SH, O−, S−, $OR_d$ or $SR_d$; $R_c$ is OH, SH, O−, S−, $OR_d$, $SR_d$, alkyl, alkoxy, alkylether, alkoxyalkylether, phosphate, thiophosphate, phosphoalkyl, thiophosphoalkyl, phosphoalkylether or thiophosphoalkylether; and $R_d$ is a counter ion;

$R^4$ is, at each occurrence, independently OH, SH, O−, S−, $OR_d$ or $SR_d$;

$R^5$ is, at each occurrence, independently oxo, thioxo or absent;

Q is, at each occurrence, independently a moiety comprising a reactive group capable of forming a covalent bond with an analyte molecule, a solid support or a complementary reactive group Q';

m is, at each occurrence, independently an integer of zero or greater; and n is an integer of one or greater.

In some embodiments, at least one occurrence of m is an integer of one or greater. In other embodiments, at least one occurrence of m is an integer of two or greater. In still different embodiments, at least one occurrence of m is an integer of three or greater. In still different embodiments, at least one occurrence of m is an integer of four or greater. In still different embodiments, at least one occurrence of m is an integer of five or greater.

The various linkers and substituents (e.g., M, Q, $R^1$, $R^2$, $R^3$, $R_c$ $L^1$, $L^2$, $L^3$ and $L^4$) in the compound of structure (I) are optionally substituted with one more substituent. For example, in some embodiments the optional substituent is selected to optimize the water solubility or other property of the compound of structure (I). In certain embodiments, each alkyl, alkoxy, alkylether, alkoxyalkylether, phosphoalkyl, thiophosphoalkyl, phosphoalkylether and thiophosphoalkylether in the compound of structure (I) is optionally substituted with one more substituent selected from the group consisting of hydroxyl, alkoxy, alkylether, alkoxyalkylether, sulfhydryl, amino, alkylamino, carboxyl, phosphate, thiophosphate, phosphoalkyl, thiophosphoalkyl, phosphoalkylether and thiophosphoalkylether.

The linker $L^1$ can be used as a point of attachment of the M moiety to the remainder of the compound. For example, in some embodiments a synthetic precursor to the compound of structure (I) is prepared, and the M moiety is attached to the synthetic precursor using any number of facile methods known in the art, for example methods referred to as "click chemistry." For this purpose any reaction which is rapid and substantially irreversible can be used to attach M to the synthetic precursor to form a compound of structure (I). Exemplary reactions include the copper catalyzed reaction of an azide and alkyne to form a triazole (Huisgen 1, 3-dipolar cycloaddition), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse-demand Diels-Alder, alkene and tetrazole photoreaction and various displacement reactions, such as displacement of a leaving group by nucleophilic attack on an electrophilic atom. In some embodiments the reaction to form $L^1$ may be performed in an aqueous environment.

Accordingly, in some embodiments $L^1$ is a functional group which is the product of one of the foregoing "click" reactions. In various embodiments, for at least one occurrence of $L^1$, the functional group can be formed by reaction of an aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin or thiirane functional group with a complementary reactive group.

In other embodiments, for at least one occurrence of $L^1$, the functional group can be formed by reaction of an alkyne and an azide.

In more embodiments, for at least one occurrence of $L^1$, the functional group comprises an alkene, ester, amide, thioester, disulfide, carbocyclic, heterocyclic or heteroaryl group. In some more specific embodiments, for at least one occurrence of $L^1$, $L^1$ is a linker comprising a triazolyl functional group.

In still other embodiments, for at least one occurrence of $L^1$, $L^1$-M has the following structure:

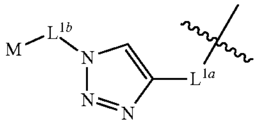

wherein $L^{1a}$ and $L^{1b}$ are each independently optional linkers.

In different embodiments, for at least one occurrence of $L^1$, $L^1$-M has the following structure:

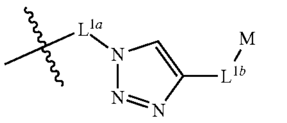

wherein $L^{1a}$ and $L^{1b}$ are each independently optional linkers.

Accordingly, in some embodiments the compound has the following structure (IA):

(IA)

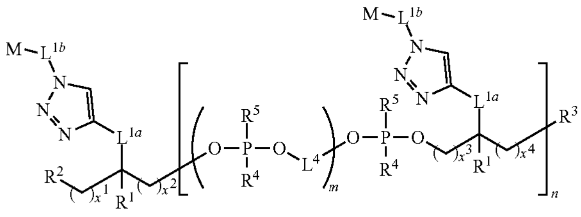

wherein:

$L^{1a}$ and $L^{1b}$ are, at each occurrence, independently optional linkers; and $x^1$, $x^2$, $x^3$ and $x^4$ are, at each occurrence, independently an integer from 0 to 6.

In different embodiments, the compound has the following structure (IB):

(IB)

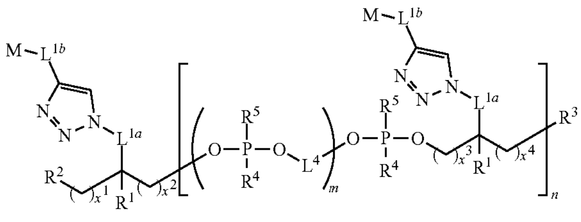

wherein:

$L^{1a}$ and $L^{1b}$ are, at each occurrence, independently optional linkers; and $x^1$, $x^2$, $x^3$ and $x^4$ are, at each occurrence, independently an integer from 0 to 6.

In various embodiments of the foregoing, $L^{1a}$ or $L^{1b}$, or both, is absent. In other embodiments, $L^{1a}$ or $L^{1b}$, or both, is present.

In some embodiments $L^{1a}$ and $L^{1b}$, when present, are each independently alkylene or heteroalkylene. For example, in some embodiments $L^{1a}$ and $L^{1b}$, when present, independently have one of the following structures:

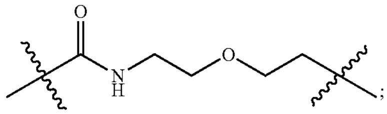
;

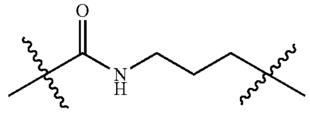
or

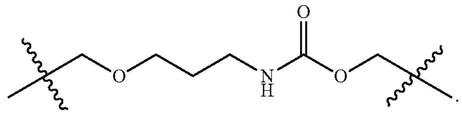
.

In more embodiments, $L^2$, $L^3$ and $L^4$ are, at each occurrence, independently $C_1$-$C_6$ alkylene, $C_2$-$C_6$ alkenylene or $C_2$-$C_6$ alkynylene. In other embodiments, $L^4$ is, at each occurrence, independently $C_1$-$C_6$ alkylene, $C_2$-$C_6$ alkenylene or $C_2$-$C_6$ alkynylene. For example, in some embodiments the compound has the following structure (IC):

(IC)

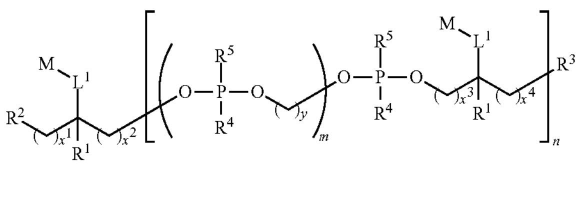

wherein:

$x^1$, $x^2$, $x^3$ and $x^4$ are, at each occurrence, independently an integer from 0 to 6; and y is, at each occurrence, independently an integer from 1 to 6.

In some embodiments of structure (IC), $L^1$, at each occurrence, independently comprises a triazolyl functional group. In other embodiments of (IC), y is 2 for each integral value of m.

In certain embodiments of the compound of structure (IC), $x^3$ and $x^4$ are both 2 at each occurrence. In other embodiments, $x^1$, $x^2$, $x^5$ and $x^6$ are each 1 at each occurrence. In different embodiments, $x^2$ and $x^4$ are each 0, and $x^3$ is 1.

In still other embodiments of any of the foregoing compounds of structure (I), $R^4$ is, at each occurrence, independently OH, $O^-$ or $OR_d$. It is understood that "$OR_d$" and "$SR_d$" are intended to refer to $O^-$ and $S^-$ associated with a cation. For example, the disodium salt of a phosphate group may be represented as:

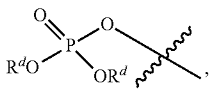
, where $R_a$ is sodium ($Na^+$).

In other embodiments of any of the compounds of structure (I), $R^5$ is, at each occurrence, oxo.

In still different embodiments, the compound has one of the following structures (ID) or (IE):

(ID)

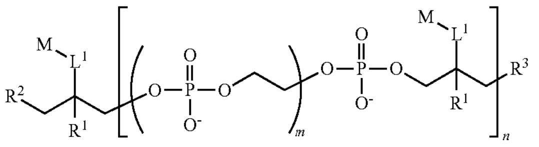

or (IE)

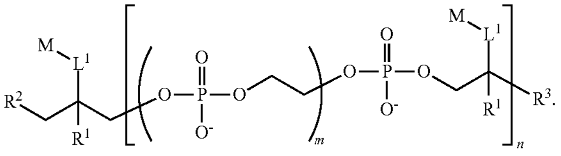

In some specific embodiments of (ID) and (IE), $L^1$, at each occurrence, independently comprises a triazolyl functional group.

In some different embodiments of any of the foregoing compounds, $R^1$ is H.

In other various embodiments, $R^2$ and $R^3$ are each independently OH or —OP(═$R_a$)($R_b$)$R_c$. In some different embodiments, $R^2$ or $R^3$ is OH or —OP(═$R_a$)(R)$R_c$, and the other of $R^2$ or $R^3$ is Q or a linker comprising a covalent bond to Q.

In still other embodiments, Q is, at each occurrence, independently a moiety comprising a reactive group capable of forming a covalent bond with an analyte molecule or a solid support. In other embodiments, Q is, at each occurrence, independently a moiety comprising a reactive group capable of forming a covalent bond with a complementary reactive group Q'. For example, in some embodiments, Q' is present on a further compound of structure (I) (e.g., in the $R^2$ or $R^3$ position), and Q and Q' comprise complementary reactive groups such that reaction of the compound of structure (I) and the further compound of structure (I) results in covalently bound dimer of the compound of structure (I). Multimer compounds of structure (I) can also be prepared in an analogous manner and are included within the scope of embodiments of the invention.

The type of Q group and connectivity of the Q group to the remainder of the compound of structure (I) is not limited, provided that Q comprises a moiety having appropriate reactivity for forming the desired bond.

In certain embodiments, the Q is a moiety which is not susceptible to hydrolysis under aqueous conditions, but is sufficiently reactive to form a bond with a corresponding group on an analyte molecule or solid support (e.g., an amine, azide or alkyne).

Certain embodiments of compounds of structure (I) comprises Q groups commonly employed in the field of bioconjugation. For example in some embodiments, Q comprises a nucleophilic reactive group, an electrophilic reactive group or a cycloaddition reactive group. In some more specific embodiments, Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group. In some embodiments, the activated ester is an N-succinimide ester, imidoester or polyflourophenyl ester. In other embodiments, the alkyne is an alkyl azide or acyl azide.

Exemplary Q moieties are provided in Table I below.

TABLE 1

| Exemplary Q Moieties | |
|---|---|
| Structure | Class |
| 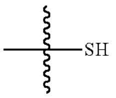 [SMILES: *S] | Sulfhydryl |
| 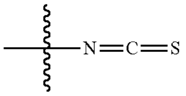 [SMILES: *N=C=S] | Isothiocyanate |
| 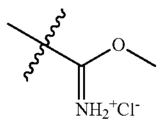 | Imidoester |
| 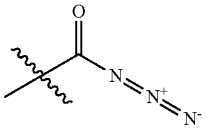 [SMILES: *C(=O)N=[N+]=[N-]] | Acyl Azide |
| 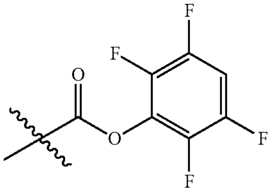 [SMILES: *C(=O)Oc1c(F)c(F)cc(F)c1F] | Activated Ester |
| 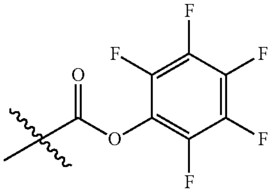 [SMILES: *C(=O)Oc1c(F)c(F)c(F)c(F)c1F] | Activated Ester |
| 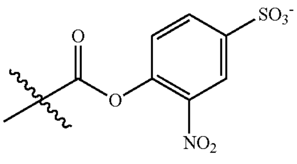 | Activated Ester |
| 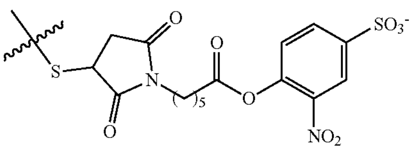 | Activated Ester |
| 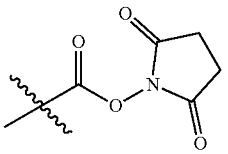 [SMILES: *C(=O)ON1C(=O)CCC1=O] | Activated Ester |

TABLE 1-continued

| Exemplary Q Moieties | |
|---|---|
| Structure | Class |
| 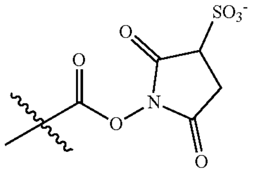 | Activated Ester |
| 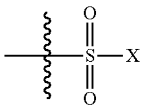 X = halo | Sulfonyl halide |
| 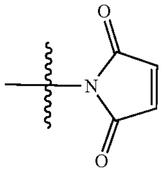 [SMILES: *N1C(=O)C=CC1=O] | Maleimide |
| 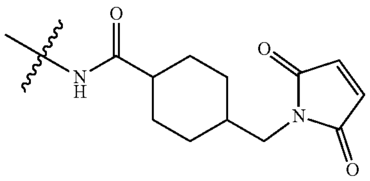 [SMILES: *NC(=O)C1CCC(CN2C(=O)C=CC2=O)CC1] | Maleimide |
| 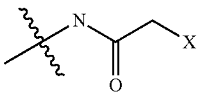 X = halo | α-haloimide |
| 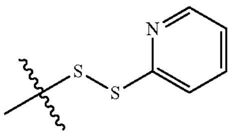 [SMILES: *SSc1ccccn1] | Disulfide |
| 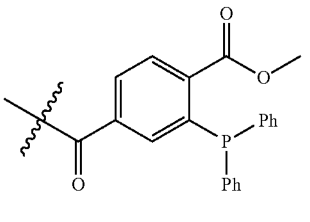 [SMILES: *C(=O)c1ccc(C(=O)OC)c(P(c2ccccc2)c2ccccc2)c1] | Phosphine |
| 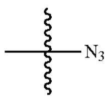 [SMILES: *N=[N+]=[N-]] | Azide |
| 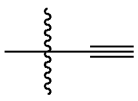 [SMILES: *C#C] | Alkyne |

TABLE 1-continued

| Exemplary Q Moieties | |
|---|---|
| Structure | Class |
| 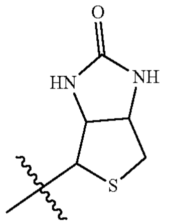 [SMILES: *C1SCC2NC(=O)NC21] | Biotin |
| 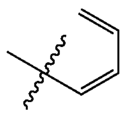 | Diene |
| 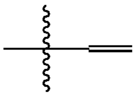 [SMILES: *C=C] | Alkene/ dienophile |
| 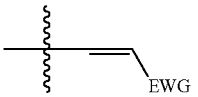 EWG = electron withdrawing group | Alkene/ dienophile |
| $—NH_2$ | Amino |

It should be noted that in some embodiments, wherein Q is SH, the SH moiety will tend to form disulfide bonds with another sulfhiydryl group on another compound of structure (I). Accordingly, some embodiments include compounds of structure (I), which are in the form of disulfide dimers, the disulfide bond being derived from SH Q groups.

In some other embodiments, one of $R^2$ or $R^3$ is OH or $—OP(=R_a)(R_b)R_c$, and the other of $R^2$ or $R^3$ is a linker comprising a covalent bond to an analyte molecule or a linker comprising a covalent bond to a solid support. For example, in some embodiments the analyte molecule is a nucleic acid, amino acid or a polymer thereof. In other embodiments, the analyte molecule is an enzyme, receptor, receptor ligand, antibody, glycoprotein, aptamer or prion. In still different embodiments, the solid support is a polymeric bead or nonpolymeric bead.

The value for m is another variable that can be selected based on the desired fluorescence and/or color intensity. In some embodiments, m is, at each occurrence, independently an integer from 1 to 10, 3 to 10 or 7 to 9. In other embodiments, m is, at each occurrence, independently an integer from 1 to 5, for example 1, 2, 3, 4 or 5. In other embodiments, m is, at each occurrence, independently an integer from 5 to 10, for example 5, 6, 7, 8, 9 or 10. In other embodiments, each occurrence of m is an integer of one or greater. For example, in some embodiments each occurrence of m is an integer of two or greater or three or greater.

The fluorescence intensity can also be tuned by selection of different values of n. In certain embodiments, n is an integer from 1 to 100. In other embodiments, n is an integer from 1 to 10. In some embodiments, n is 1.

M is selected based on the desired optical properties, for example based on a desired color and/or fluorescence emission wavelength. In some embodiments, M is the same at each occurrence; however, it is important to note that each occurrence of M need not be an identical M, and certain embodiments include compounds wherein M is not the same at each occurrence. For example, in some embodiments each M is not the same and the different M moieties are selected to have absorbance and/or emissions for use in fluorescence resonance energy transfer (FRET) methods. For example, in such embodiments the different M moieties are selected such that absorbance of radiation at one wavelength causes emission of radiation at a different wavelength by a FRET mechanism. Exemplary M moieties can be appropriately selected by one of ordinary skill in the art based on the desired end use. Exemplary M moieties for FRET methods include fluorescein and 5-TAMRA (5-carboxytetramethylrhodamine, succinimidyl ester) dyes.

M may be attached to the remainder of the molecule from any position (i.e., atom) on M. One of skill in the art will recognize means for attaching M to the remainder of molecule. Exemplary methods include the "click" reactions described herein.

In some embodiments, M is a fluorescent or colored moiety. Any fluorescent and/or colored moiety may be used, for examples those known in the art and typically employed in colorimetric, UV, and/or fluorescent assays may be used. Examples of M moieties which are useful in various embodiments of the invention include, but are not limited to: Xanthene derivatives (e.g., fluorescein, rhodamine, Oregon green, eosin or Texas red); Cyanine derivatives (e.g., cyanine, indocarbocyanine, oxacarbocyanine, thiacarbocyanine or merocyanine); Squaraine derivatives and ring-substituted squaraines, including Seta, SeTau, and Square dyes; Naphthalene derivatives (e.g., dansyl and prodan derivatives); Coumarin derivatives; oxadiazole derivatives (e.g., pyridyloxazole, nitrobenzoxadiazole or benzoxadiazole); Anthracene derivatives (e.g., anthraquinones, including DRAQ5, DRAQ7 and CyTRAK Orange); Pyrene derivatives such as cascade blue; Oxazine derivatives (e.g., Nile red, Nile blue, cresyl violet, oxazine 170); Acridine derivatives (e.g., proflavin, acridine orange, acridine yellow); Arylmethine derivatives: auramine, crystal violet, malachite green; and Tetrapyrrole derivatives (e.g., porphin, phthalocyanine or bilirubin). Other exemplary M moieties include: Cyanine dyes, xanthate dyes (e.g., Hex, Vic, Nedd, Joe or Tet); Yakima yellow; Redmond red; tamra; texas red and Alexa Fluor® dyes.

In still other embodiments of any of the foregoing, M comprises three or more aryl or heteroaryl rings, or combinations thereof, for example four or more aryl or heteroaryl rings, or combinations thereof, or even five or more aryl or heteroaryl rings, or combinations thereof. In some embodiments, M comprises six aryl or heteroaryl rings, or combinations thereof. In further embodiments, the rings are fused. For example in some embodiments, M comprises three or more fused rings, four or more fused rings, five or more fused rings, or even six or more fused rings.

In some embodiments, M is cyclic. For example, in some embodiments M is carbocyclic. In other embodiment, M is heterocyclic. In still other embodiments of the foregoing, M, at each occurrence, independently comprises an aryl moiety. In some of these embodiments, the aryl moiety is multicyclic. In other more specific examples, the aryl moiety is a fused-multicyclic aryl moiety, for example which may comprise at least 3, at least 4, or even more than 4 aryl rings.

In other embodiments of any of the foregoing compounds of structure (I), M, at each occurrence, independently comprises at least one heteroatom. For example, in some embodiments, the heteroatom is nitrogen, oxygen or sulfur.

In still more embodiments of any of the foregoing, M, at each occurrence, independently comprises at least one substituent. For example, in some embodiments the substituent is a fluoro, chloro, bromo, iodo, amino, alkylamino, arylamino, hydroxy, sulfhydryl, alkoxy, aryloxy, phenyl, aryl, methyl, ethyl, propyl, butyl, isopropyl, t-butyl, carboxy, sulfonate, amide, or formyl group.

In some even more specific embodiments of the foregoing, M, at each occurrence, independently is a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, squaraine, squarylium, 9, 10-ethynylanthracene or ter-naphthyl moiety. In other embodiments, M is, at each occurrence, independently p-terphenyl, perylene, azobenzene, phenazine, phenanthroline, acridine, thioxanthrene, chrysene, rubrene, coronene, cyanine, perylene imide, or perylene amide or a derivative thereof. In still more embodiments, M is, at each occurrence, independently a coumarin dye, resorufin dye, dipyrrometheneboron difluoride dye, ruthenium bipyridyl dye, energy transfer dye, thiazole orange dye, polymethine or N-aryl-1,8-naphthalimide dye.

In still more embodiments of any of the foregoing, M at each occurrence is the same. In other embodiments, each M is different. In still more embodiments, one or more M is the same and one or more M is different.

In some embodiments, M is pyrene, perylene, perylene monoimide or 6-FAM or derivative thereof. In some other embodiments, M has one of the following structures:

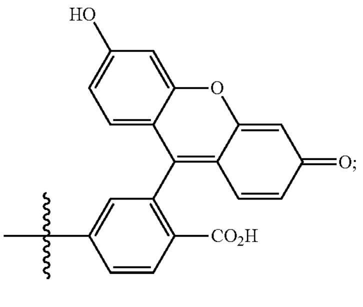;

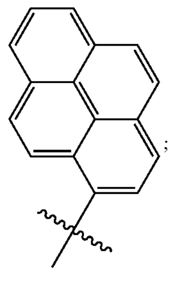;

-continued
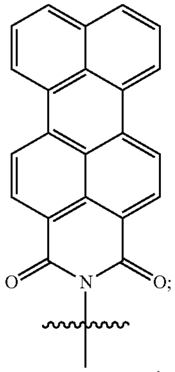
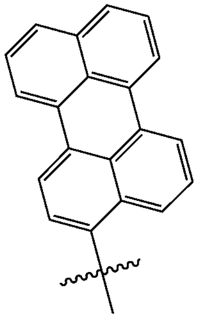
;
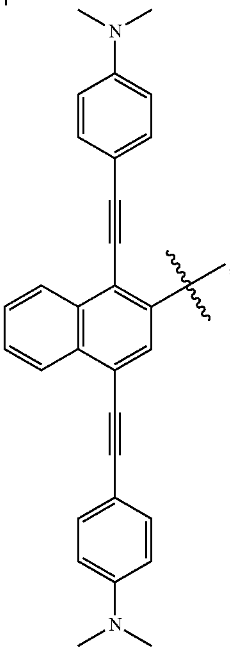
;
-continued
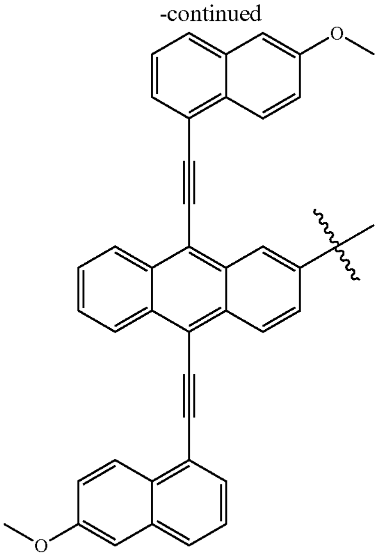
or
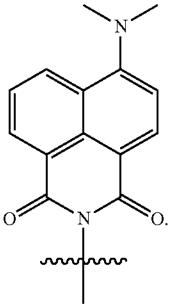 [SMILES: *N1C(=O)c2cccc3c(N(C)C)ccc(c23)C1=O]
In some specific embodiments, the compound of structure (I) is a compound selected from Table 2:
TABLE 2
| Exemplary Compounds of Structure I | |
|---|---|
| Name | Structure |
| I-1 | 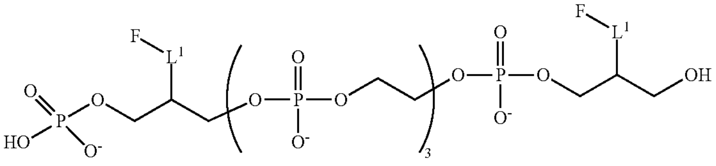 |
| I-2 | 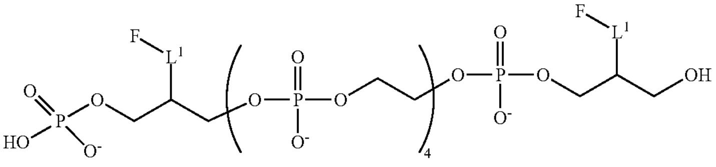 |
| I-3 | 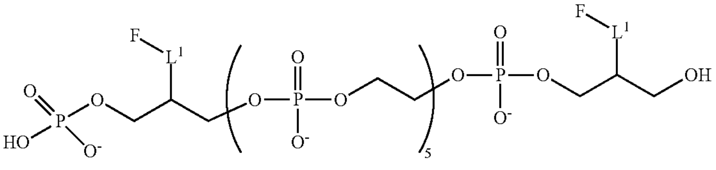 |

TABLE 2-continued
| Exemplary Compounds of Structure I | |
|---|---|
| Name | Structure |
| I-4 | 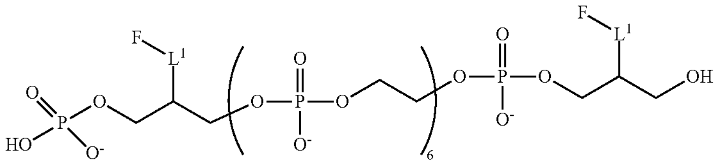 |
| I-5 | 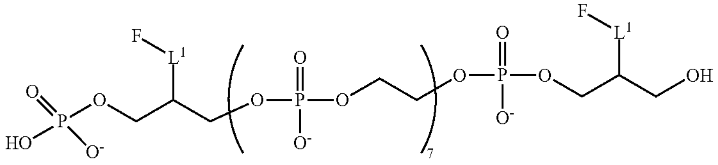 |
| I-6 | 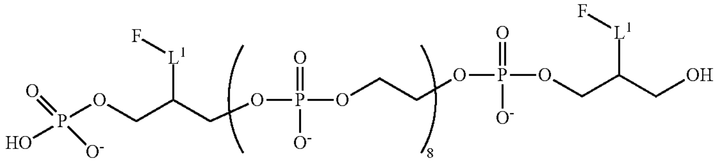 |
| I-7 | 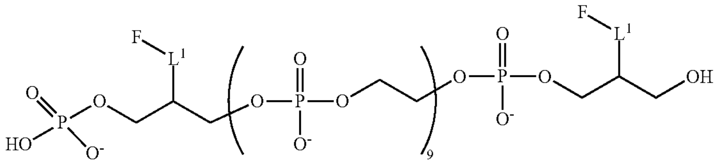 |
| I-8 | 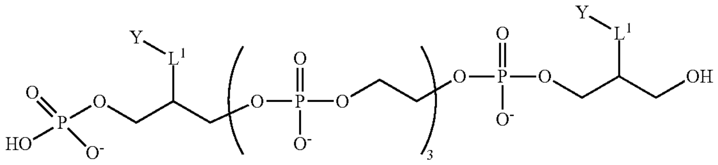 |
| I-9 | 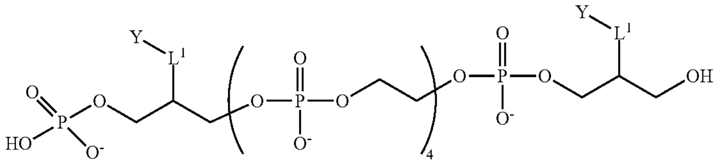 |
| I-10 | 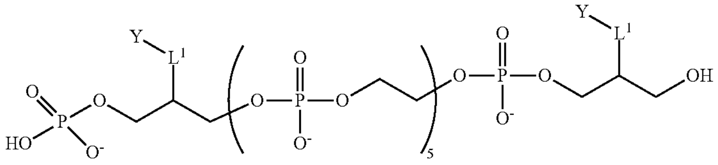 |
| I-11 | 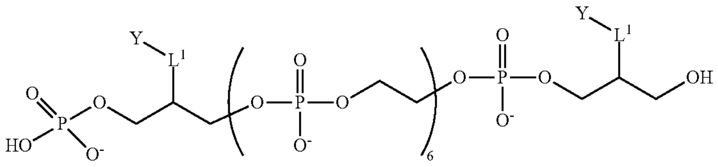 |

TABLE 2-continued
| Exemplary Compounds of Structure I | |
|---|---|
| Name | Structure |
| I-12 | 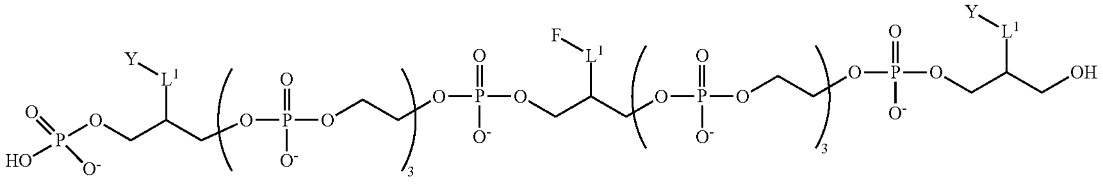 |
| I-13 | 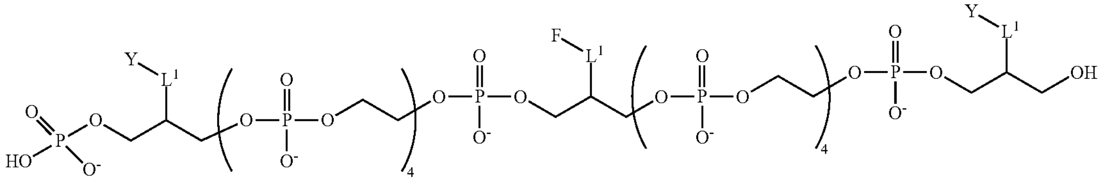 |
| I-14 | 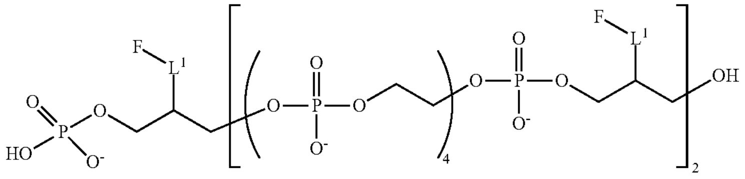 |
| I-15 | 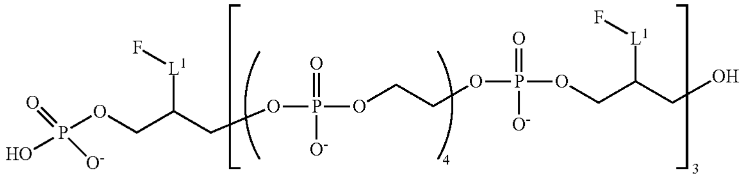 |
| I-16 | 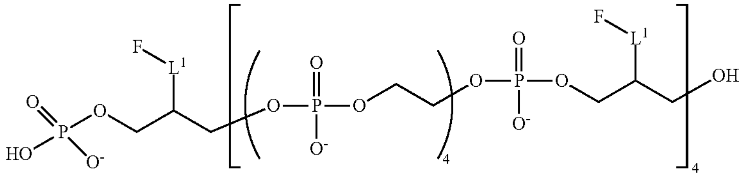 |
| I-17 | 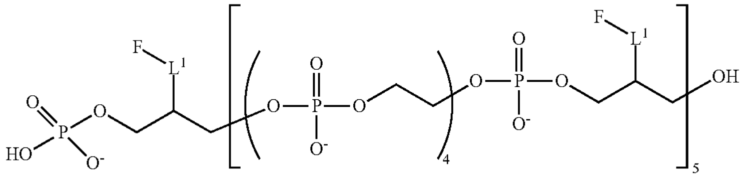 |
| I-18 | 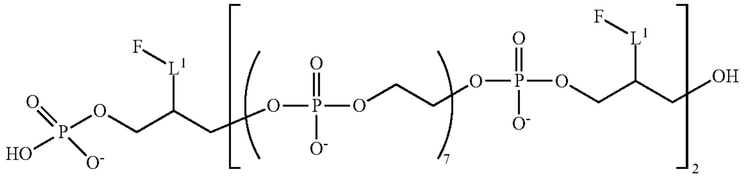 |
| I-19 | 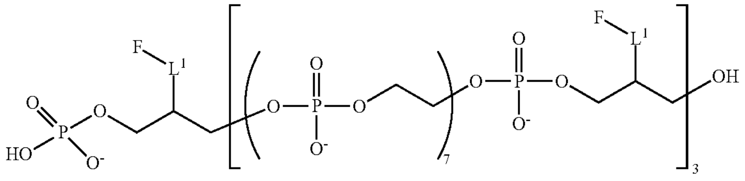 |

TABLE 2-continued
| Exemplary Compounds of Structure I | |
|---|---|
| Name | Structure |
| I-20 | 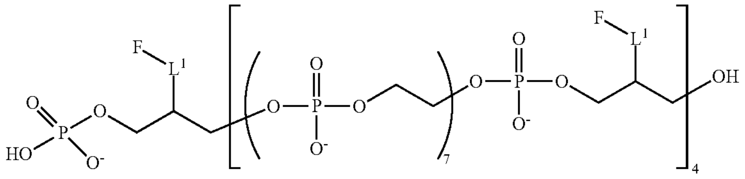 |
| I-21 | 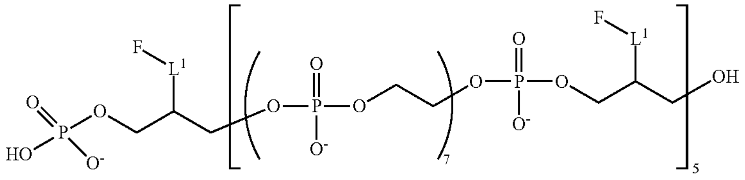 |
| I-22 | 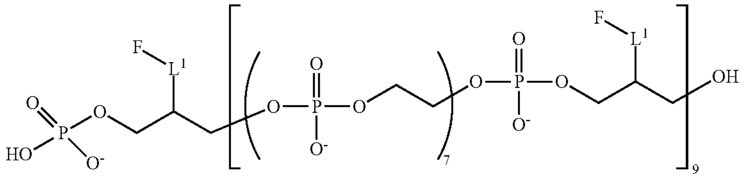 |
| I-23 | 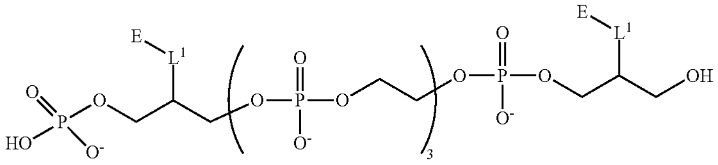 |
| I-24 | 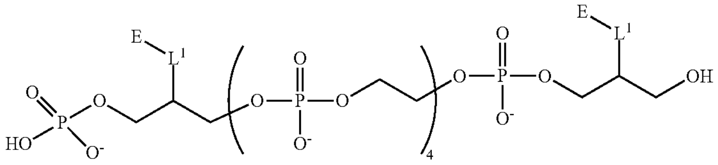 |
| I-25 | 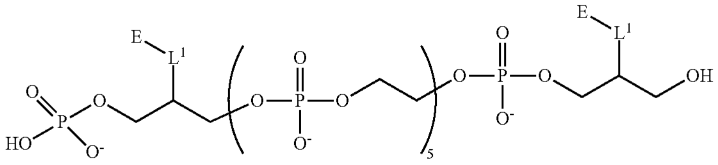 |
| I-26 | 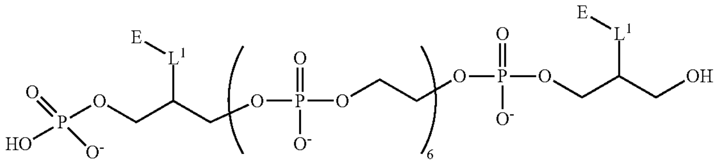 |
| I-27 | 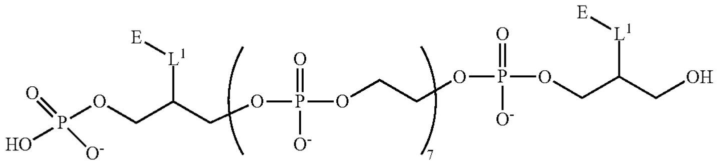 |

TABLE 2-continued
Exemplary Compounds of Structure I
| Name | Structure |
| --- | --- |
| I-28 | 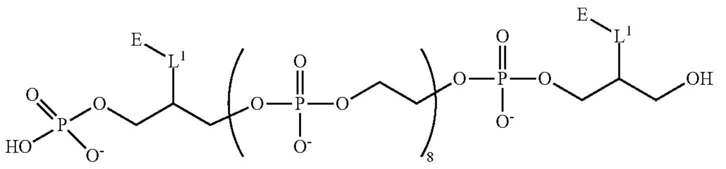 |
| I-29 | 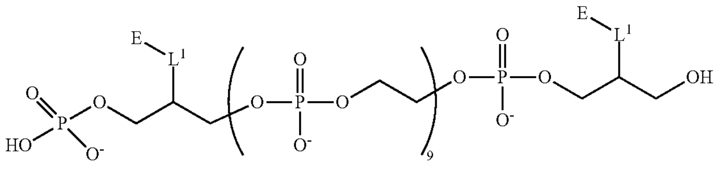 |
| I-30 | 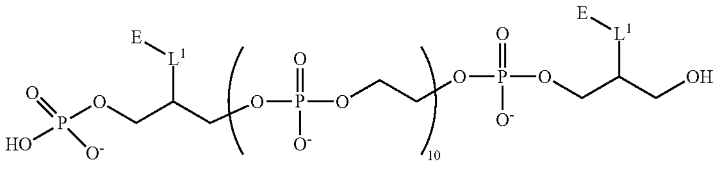 |
| I-31 | 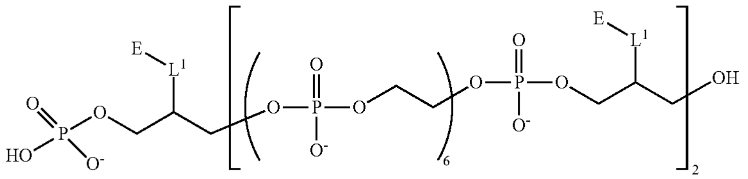 |
| I-32 | 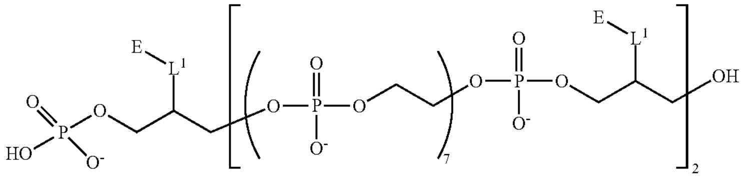 |
| I-33 | 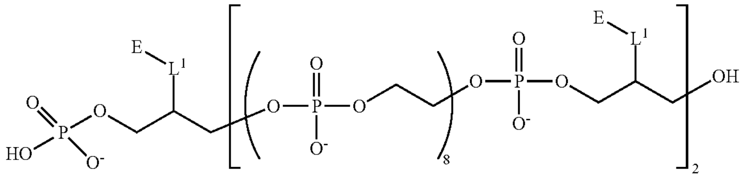 |
| I-34 | 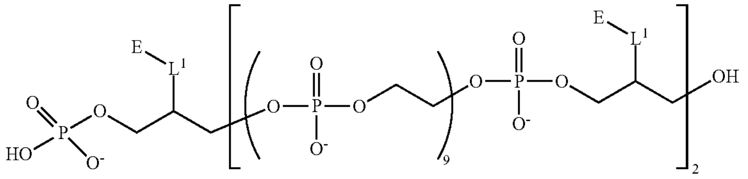 |
| I-35 | 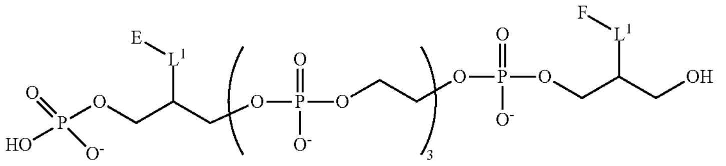 |

TABLE 2-continued

| Exemplary Compounds of Structure I | |
|---|---|
| Name | Structure |
| I-36 | 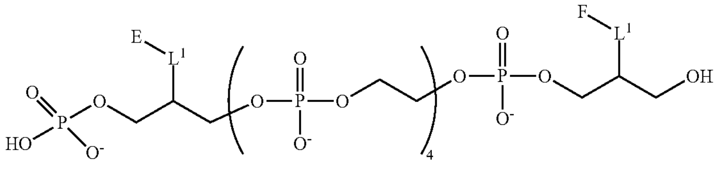 |
| I-37 | 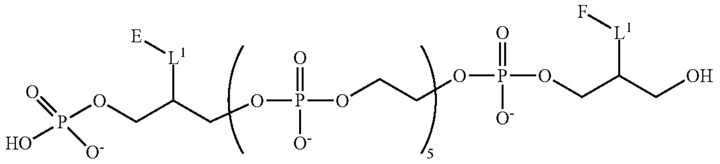 |
| I-38 | 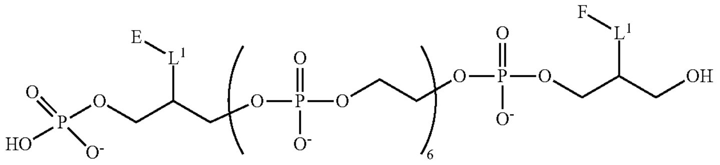 |

As used in Table 2, and throughout the application, F, E and Y refer to fluorescein, perylene and pyrene moieties, respectively, and have the following structures:

"F"

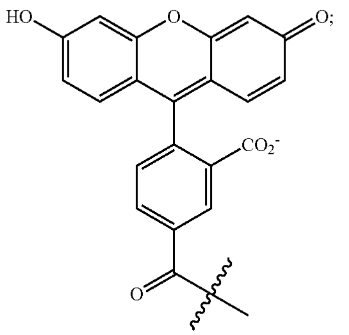

"E"

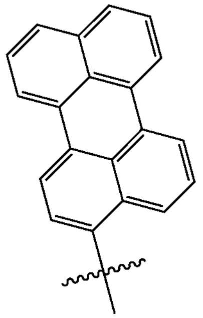

and

-continued

"Y"

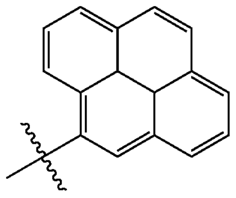

$L^1$ in the compounds of Table 2 is as defined herein for any compound of structure (I). In some specific embodiments, $L^1$ in the compounds of Table 1 is a moiety comprising a triazolyl group, the triazolyl being formed by reaction of an alkyne and an azide.

The presently disclosed dye compounds are "tunable," meaning that by proper selection of the variables in any of the foregoing compounds, one of skill in the art can arrive at a compound having a desired and/or predetermined molar fluorescence (molar brightness). The tunability of the compounds allows the user to easily arrive at compounds having the desired fluorescence and/or color for use in a particular assay or for identifying a specific analyte of interest. Although all variables may have an effect on the molar fluorescence of the compounds, proper selection of M, m and n is believed to play an important role in the molar fluorescence of the compounds. Accordingly, in one embodiment is provided a method for obtaining a compound having a desired molar fluorescence, the method comprising selecting an M moiety having a known fluorescence, preparing a compound of structure (I) comprising the M moiety, and selecting the appropriate variables for m and n to arrive at the desired molar fluorescence.

Molar fluorescence in certain embodiments can be expressed in terms of the fold increase or decrease relative to the fluorescence emission of the parent fluorophore (e.g., monomer). In some embodiments the molar fluorescence of the present compounds is 1.1×, 1.5×, 2×, 3×, 4×, 5×, 6×, 7×, 8×, 9×10× or even higher relative to the parent fluorophore.

Various embodiments include preparing compounds having the desired fold increase in fluorescence relative to the parent fluorophore by proper selection of m and n.

For ease of illustration, various compounds comprising phosphorous moieties (e.g., phosphate and the like) are depicted in the anionic state (e.g., —OPO(OH)O—, $—OPO_3^{2-}$). One of skill in the art will readily understand that the charge is dependent on pH and the uncharged (e.g., protonated or salt, such as sodium or other cation) forms are also included in the scope of embodiments of the invention.

Compositions comprising any of the foregoing compounds and one or more analyte molecules (e.g., biomolecules) are provided in various other embodiments. In some embodiments, use of such compositions in analytical methods for detection of the one or more analyte molecules are also provided.

In still other embodiments, the compounds are useful in various analytical methods. For example, in certain embodiments the disclosure provides a method of staining a sample, the method comprising adding to said sample a compound of structure (I), for example wherein one of $R^2$ or $R^3$ is a linker comprising a covalent bond to an analyte molecule (e.g., biomolecule) or microparticle, and the other of $R^2$ or $R^3$ is H, OH, alkyl, alkoxy, alkylether or $—OP(=R_a)(R_b)R_c$, in an amount sufficient to produce an optical response when said sample is illuminated at an appropriate wavelength.

In some embodiments of the foregoing methods, $R^2$ is a linker comprising a covalent linkage to an analyte molecule, such as a biomolecule. For example, a nucleic acid, amino acid or a polymer thereof (e.g., polynucleotide or polypeptide). In still more embodiments, the biomolecule is an enzyme, receptor, receptor ligand, antibody, glycoprotein, aptamer or prion.

In yet other embodiments of the foregoing method, $R^2$ is a linker comprising a covalent linkage to a solid support such as a microparticle. For example, in some embodiments the microparticle is a polymeric bead or nonpolymeric bead.

In even more embodiments, said optical response is a fluorescent response.

In other embodiments, said sample comprises cells, and some embodiments further comprise observing said cells by flow cytometry.

In still more embodiments, the method further comprises distinguishing the fluorescence response from that of a second fluorophore having detectably different optical properties.

In other embodiments, the disclosure provides a method for visually detecting an analyte molecule, such as a biomolecule, comprising:

(a) providing a compound of structure (I), for example, wherein one of $R^2$ or $R^3$ is a linker comprising a covalent bond to the analyte molecule, and the other of $R^2$ or $R^3$ is H, OH, alkyl, alkoxy, alkylether or $—OP(=R_a)(R_b)R_c$; and (b) detecting the compound by its visible properties.

In some embodiments the analyte molecule is a nucleic acid, amino acid or a polymer thereof (e.g., polynucleotide or polypeptide). In still more embodiments, the analyte molecule is an enzyme, receptor, receptor ligand, antibody, glycoprotein, aptamer or prion.

In other embodiments, a method for visually detecting an analyte molecule, such as a biomolecule is provided, the method comprising:

(a) admixing any of the foregoing compounds with one or more analyte molecules; and (b) detecting the compound by its visible properties.

In other embodiments is provided a method for visually detecting an analyte molecule, the method comprising:

(a) admixing the compound of claim 1, wherein $R^2$ or $R^3$ is Q or a linker comprising a covalent bond to Q, with the analyte molecule;

(b) forming a conjugate of the compound and the analyte molecule; and (c) detecting the conjugate by its visible properties.

In some other different embodiments, the compounds of structure (I) can be used in various for analysis of cells. For example, by use of flow cytometry, the compounds can be used to discriminate between live and dead cells, evaluate the health of cells (e.g., necrosis vs. early apoptitic vs. late apoptitic vs. live cell), tracking ploidy and mitosis during the cell cycle and determining various states of cell proliferation. While not wishing to be bound by theory, it is believed that embodiments of the compounds of structure (I) preferentially bind to positively charged moieties. Accordingly, in some embodiments the compounds may be used in methods for determining the presence of non-intact cells, for example nectrotic cells. For example, the presence of nectrotic cells can be determined by admixing a sample containing cells with a compound of structure (I) and analyzing the mixture by flow cytometry. The compound of structure (I) binds to nectrotic cells, and thus there presence is detectable under flow cytometry conditions. In contrast to other staining reagents which require an amine reactive group to bind to nectrotic cells, embodiments of the staining methods of employing compounds of structure (I) do not require a protein-free incubation buffer, and thus the methods are more efficient to perform than related known methods.

In various other embodiments, the compounds can be used in related methods for determining the presence of positively charged moieties in intact or non-intact cells, apoptitic bodies, depolarized membranes and/or permealized membranes.

In addition to the above methods, embodiments of the compounds of structure (I) find utility in various disciplines and methods, including but not limited to: imaging in endoscopy procedures for identification of cancerous and other tissues; identification of necrotic tissue by preferential binding of the compounds to dead cells; single-cell and/or single molecule analytical methods, for example detection of polynucleotides with little or no amplification; cancer imaging, for example by conjugating a compound of structure (I) to an antibody or sugar or other moiety that preferentially binds cancer cells; imaging in surgical procedures; binding of histones for identification of various diseases; drug delivery, for example by replacing the M moiety in a compound of structure (I) with an active drug moiety; and/or contrast agents in dental work and other procedures, for example by preferential binding of the compound of structure (I) to various flora and/or organisms.

It is understood that any embodiment of the compounds of structure (I), as set forth above, and any specific choice set forth herein for a $R^1$, $R^2$, $R^3$, $R^4$, $R^5$, $L^1$, $L^2$, $L^3$, $L^4$, M, m and/or n variable in the compounds of structure (I), as set forth above, may be independently combined with other embodiments and/or variables of the compounds of structure (I) to form embodiments of the inventions not specifically set forth above. In addition, in the event that a list of choices is listed for any particular $R^1$, $R^2$, $R^3$, $R^4$, $R^5$, $L^1$, $L^2$, $L^3$, $L^4$, M, m and/or n variable in a particular embodiment and/or claim, it is understood that each individual choice may be deleted from the particular embodiment and/or claim and that the remaining list of choices will be considered to be within the scope of the invention.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Furthermore, all compounds of the invention which exist in free base or acid form can be converted to their salts by treatment with the appropriate inorganic or organic base or acid by methods known to one skilled in the art. Salts of the compounds of the invention can be converted to their free base or acid form by standard techniques.

The following Reaction Schemes illustrate exemplary methods of making compounds of this invention. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc., or synthesized according to sources known to those skilled in the art (see, for example, Advanced Organic Chemistry: Reactions, Mechanisms, and Structure, 5th edition (Wiley, December 2000)) or prepared as described in this invention.

Reaction Scheme I

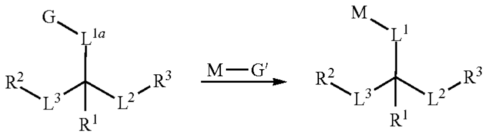

a b

Reaction Scheme I illustrates an exemplary method for preparation of intermediates useful for preparation of compounds of structure (I). Referring to reaction Scheme I, where $R^1$, $L^1$, $L^2$, $L^3$, G and M are as defined above, and $R^2$ and $R^3$ are as defined above or are protected variants thereof, a compound of structure a, which can be purchased or prepared by well-known techniques, is reacted with M-G' to yield compounds of structure b. Here, G and G' represent functional groups having complementary reactivity (i.e., functional groups which react to form a covalent bond). G' may be pendant to M or a part of the structural backbone of M. G may be any number of functional groups described herein, such as alkyne, and G' may be any of a number of functional groups, for example azide.

The compound of structure (I) may be prepared from structure b by reaction under well-known automated DNA synthesis conditions with a phosphoramidite compound having the following structure (c):

(c)

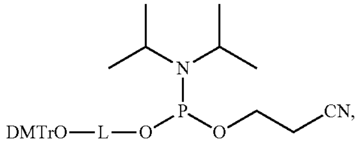

wherein L is independently an optional linker, followed by reaction with another compound of structure b. Multimer compounds of structure (I) are prepared by reacting the desired number of compounds of structure b sequentially with the appropriate phosphoramidite reagent under DNA synthesis conditions.

Alternatively, the compounds of structure (I) are prepared by first synthesizing an simeric or oligomeric compound have the following structure d under typical DNA synthesis conditions:

(d)

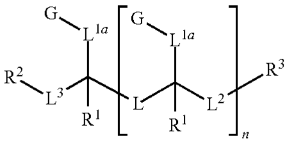

wherein G, $L^{1a}$, $L^2$, $L^3$, $R^1$, $R^2$, $R^3$ and n are as defined herein for compounds of structure (II), and then reacting the compound of structure d with M-$L^{1b}$-G', wherein M, $L^{1b}$ and G' are defined herein for compounds of structure (II) and related methods.

DNA synthesis methods are well-known in the art. Briefly, two alcohol groups, for example $R^2$ and $R^3$ in intermediates b or d above, are functionalized with a dimethoxytrityl (DMT) group and a 2-cyanoethyl-N,N-diisopropylamino phosphoramidite group, respectively. The phosphoramidite group is coupled to an alcohol group, typically in the presence of an activator such as tetrazole, followed by oxidation of the phosphorous atom with iodine. The dimethoxytrityl group can be removed with acid (e.g., chloroacetic acid) to expose the free alcohol, which can be reacted with a phosphoramidite group. The 2-cyanoethyl group can be removed after oligomerization by treatment with aqueous ammonia.

Preparation of the phosphoramidites used in the oligomerization methods is also well-known in the art. For example, a primary alcohol (e.g., $R^3$) can be protected as a DMT group by reaction with DMT-Cl. A secondary alcohol (e.g., $R^2$) is then functionalized as a phosphoramidite by reaction with an appropriate reagent such as 2-cyanoethyl N,N- dissopropylchlorophosphoramidite. Methods for preparation of phosphoramidites and their oligomerization are well-known in the art and described in more detail in the examples.

Compounds of structure (I) are prepared by oligomerization of intermediate b according to the well-known phophoramidite chemistry described above. The desired number of m and n repeating units is incorporated into the molecule by repeating the phosphoramidite coupling the desired number of times. It will be appreciated that compounds of structure (II) as, described below, can be prepared by analogous methods.

In various other embodiments, compounds useful for preparation of the compound of structure (I) are provided. The compounds can be prepared above in monomer, dimer and/or oligomeric form and then the M moiety covalently attached to the compound via any number of synthetic methodologies (e.g., the "click" reactions described above) to form a compound of structure (I). Accordingly, in various embodiments a compound is provided having the following structure (II):

(II)

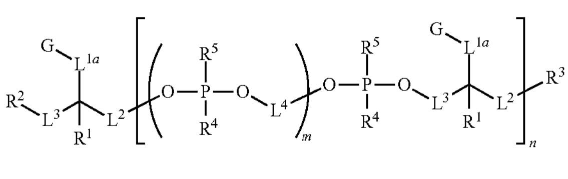

or a stereoisomer, salt or tautomer thereof, wherein:

- G is, at each occurrence, independently a moiety comprising a reactive group capable of forming a covalent bond with a complementary reactive group;
- $L^{1a}$, $L^2$ and $L^3$ are, at each occurrence, independently an optional alkylene, alkenylene, alkynylene, heteroalkylene, heteroalkenylene, heteroalkynylene or heteroatomic linker;
- $L^4$ is, at each occurrence, independently an alkylene, alkenylene, alkynylene, heteroalkylene, heteroalkenylene or heteroalkynylene linker;
- $R^1$ is, at each occurrence, independently H, alkyl or alkoxy;
- $R^2$ and $R^3$ are each independently H, OH, SH, alkyl, alkoxy, alkylether, —OP(=$R_a$)($R_b$)$R_c$, Q, a linker comprising a covalent bond to Q, a linker comprising a covalent bond to an analyte molecule, a linker comprising a covalent bond to a solid support or a linker comprising a covalent bond to a further compound of structure (II), wherein: $R_a$ is O or S; Re is OH, SH, O–, S–, $OR_d$ or $SR_d$; $R_c$ is OH, SH, $O^-$, $S^-$, $OR_d$, $SR_d$, alkyl, alkoxy, alkylether, alkoxyalkylether, phosphate, thiophosphate, phosphoalkyl, thiophosphoalkyl, phosphoalkylether or thiophosphoalkylether; and $R_d$ is a counter ion;
- $R^4$ is, at each occurrence, independently OH, SH, $O^-$, $S^-$, $OR_d$ or $SR_d$;
- $R^5$ is, at each occurrence, independently oxo, thioxo or absent;
- Q is, at each occurrence, independently a moiety comprising a reactive group capable of forming a covalent bond with an analyte molecule, a solid support or a complementary reactive group Q';
- m is, at each occurrence, independently an integer of zero or greater; and
- n is an integer of one or greater.

In some embodiments, at least one occurrence of m is an integer of one or greater. In other embodiments, at least one occurrence of m is an integer of two or greater. In still different embodiments, at least one occurrence of m is an integer of three or greater.

The G moiety in the compound of structure (II) can be selected from any moiety comprising a group having the appropriate reactivity group for forming a covalent bond with a complementary group on an M moiety. In exemplary embodiments, the G moiety can be selected from any of the Q moieties described herein, including those specific examples provided in Table 1. In some embodiments, G comprises, at each occurrence, independently a moiety suitable for reactions including: the copper catalyzed reaction of an azide and alkyne to form a triazole (Huisgen 1, 3-dipolar cycloaddition), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse-demand Diels-Alder, alkene and tetrazole photoreaction and various displacement reactions, such as displacement of a leaving group by nucleophilic attack on an electrophilic atom.

In some embodiments, G is, at each occurrence, independently a moiety comprising an aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin or thiirane functional group.

In other embodiments, G comprises, at each occurrence, independently an alkyne or an azide group. In different embodiments, G comprises, at each occurrence, independently a reactive group capable of forming a functional group comprising an alkene, ester, amide, thioester, disulfide, carbocyclic, heterocyclic or heteroaryl group, upon reaction with the complementary reactive group.

For example, in some embodiment the heteroaryl is triazolyl.

In some embodiments, the compound has the following structure (IIA):

(IIA)

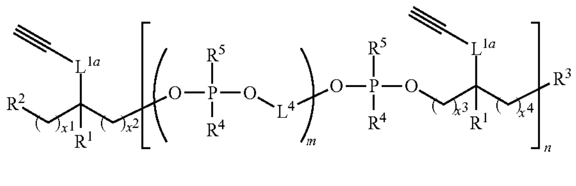

wherein:

- $L^{1a}$ and $L^{1b}$ are, at each occurrence, independently optional linkers; and
- $x^1$, $x^2$, $x^3$ and $x^4$ are, at each occurrence, independently an integer from 0 to 6.

In some specific embodiments of (II) and (IIa), each $L^{1a}$ is absent. In other embodiments each $L^{1a}$ is present. For example, in some embodiments $L^{1a}$ is, at each occurrence, independently heteroalkylene. In other embodiments, $L^{1a}$ has the following structure:

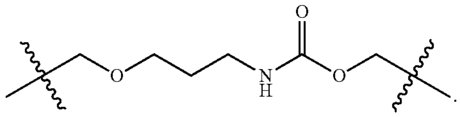 [SMILES: *COCCCNC(=O)OC*]

In various other embodiments of the compound of structure (II), $L^2$, $L^3$ $L^4$ are, at each occurrence, independently $C_1$-$C_6$ alkylene, $C_2$-$C_6$ alkenylene or $C_2$-$C_6$ alkynylene. In some other embodiments, $L^4$ is, at each occurrence, independently $C_1$-$C_6$ alkylene, $C_2$-$C_6$ alkenylene or $C_2$-$C_6$ alkynylene.

In other embodiments, the compound has the following structure (IIB):

(IIB)

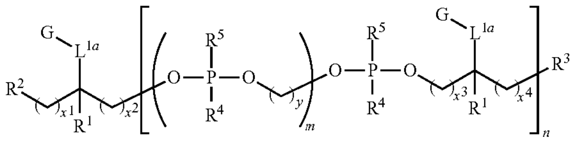

wherein:

$x^1$, $x^2$, $x^3$ and $x^4$ are, at each occurrence, independently an integer from 0 to 6; and y is an integer from 1 to 6.

In other of any of the foregoing embodiments of compound (II), G is, at each occurrence, independently or

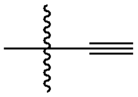 or 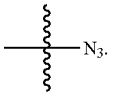

In various embodiments of the compound of structure (IIa), $x^3$ and $x^4$ are both 2 at each occurrence. In other embodiments, $x^1$, $x^2$, $x^5$ and $x^6$ are each 1 at each occurrence. In other embodiments, y is 2 for each integral value of m.

In other embodiments, $R^4$ is, at each occurrence, independently OH, $O^-$ or $OR_d$, and in different embodiments $R^5$ is, at each occurrence, oxo.

In some different embodiments, the compound has one of the following structures (IID) or (IIE):

(IID)

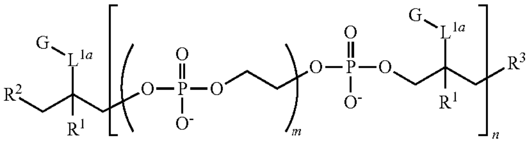 or (IIE)

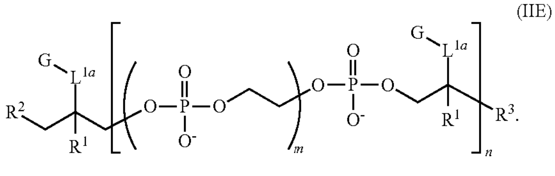

In some embodiments of any of the foregoing compounds of structure (II), G is, at each occurrence, independently

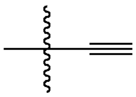 or 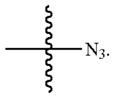

In some other different embodiments of any of the foregoing compounds of structure (II), $R^1$ is H.

In other various embodiments of the compounds of structure (II), $R^2$ and $R^3$ are each independently OH or —OP(═$R_a$)($R_b$)$R_c$. In some different embodiments, $R^2$ or $R^3$ is OH or —OP(═$R_a$)($R_b$)$R_c$, and the other of $R^2$ or $R^3$ is Q or a linker comprising a covalent bond to Q.

In still other embodiments of compounds of structure (II), Q is, at each occurrence, independently a moiety comprising a reactive group capable of forming a covalent bond with an analyte molecule or a solid support. In other embodiments, Q is, at each occurrence, independently a moiety comprising a reactive group capable of forming a covalent bond with a complementary reactive group Q'. For example, in some embodiments, Q' is present on a further compound of structure (II) (e.g., in the $R^2$ or $R^3$ position), and Q and Q' comprise complementary reactive groups such that reaction of the compound of structure (II) and the further compound of structure (II) results in covalently bound dimer of the compound of structure (II). Multimer compounds of structure (II) can also be prepared in an analogous manner and are included within the scope of embodiments of the invention.

The type of Q group and connectivity of the Q group to the remainder of the compound of structure (II) is not limited, provided that Q comprises a moiety having appropriate reactivity for forming the desired bond.

In certain embodiments of compounds of structure (II), the Q is a moiety which is not susceptible to hydrolysis under aqueous conditions, but is sufficiently reactive to form a bond with a corresponding group on an analyte molecule or solid support (e.g., an amine, azide or alkyne).

Certain embodiments of compounds of structure (II) comprises Q groups commonly employed in the field of bioconjugation. For example in some embodiments, Q comprises a nucleophilic reactive group, an electrophilic reactive group or a cycloaddition reactive group. In some more specific embodiments, Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group. In some embodiments, the activated ester is an N-succinimide ester, imidoester or polyflourophenyl ester. In other embodiments, the alkyne is an alkyl azide or acyl azide.

Exemplary Q moieties for compounds of structure (II) are provided in Table I above.

As with compounds of structure (I), in some embodiments of compounds of structure (II), wherein Q is SH, the SH moiety will tend to form disulfide bonds with another sulfhydryl group on another compound of structure (II). Accordingly, some embodiments include compounds of structure (II), which are in the form of disulfide dimers, the disulfide bond being derived from SH Q groups.

In some other embodiments of compounds of structure (II), one of $R^2$ or $R^3$ is OH or —OP(═$R_a$)($R_b$)$R_c$, and the other of $R^2$ or $R^3$ is a linker comprising a covalent bond to an analyte molecule or a linker comprising a covalent bond to a solid support. For example, in some embodiments the analyte molecule is a nucleic acid, amino acid or a polymer thereof. In other embodiments, the analyte molecule is an enzyme, receptor, receptor ligand, antibody, glycoprotein, aptamer or prion. In still different embodiments, the solid support is a polymeric bead or nonpolymeric bead.

In other embodiments of compounds of structure (II), m is, at each occurrence, independently an integer from 1 to 10, 3 to 10 or 7 to 9. In other embodiments, m is, at each occurrence, independently an integer from 1 to 5. In other embodiments, each occurrence of m is an integer of one or greater. For example, in some embodiments each occurrence of m is an integer of two or greater or three or greater.

In yet different embodiments of compounds of structure (II) n is an integer from 1 to 100. For example, in some embodiments n is an integer from 1 to 10.

In other different embodiments, the compound of structure (II) is selected from Table 3.

TABLE 3

Exemplary Compounds of Structure (II)

| Name | Structure |
|---|---|
| II-1 | 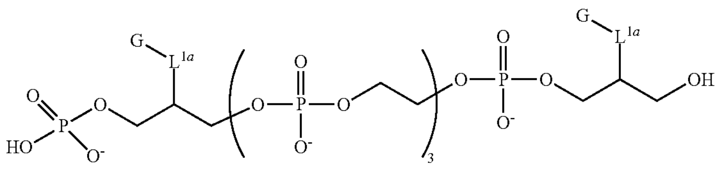 |
| II-2 | 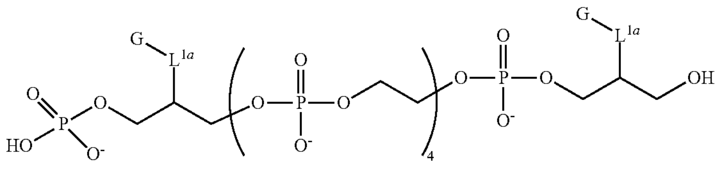 |
| II-3 | 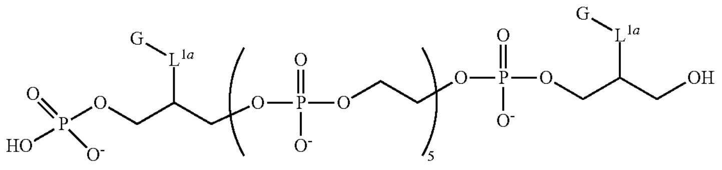 |
| II-4 | 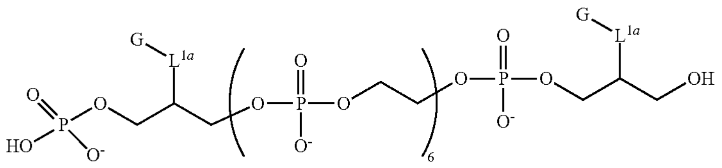 |
| II-5 | 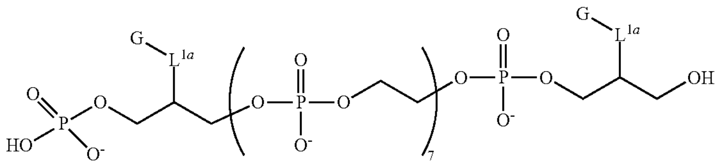 |
| II-6 | 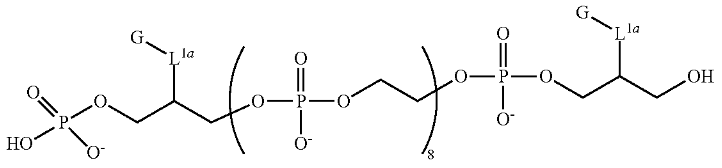 |
| II-7 | 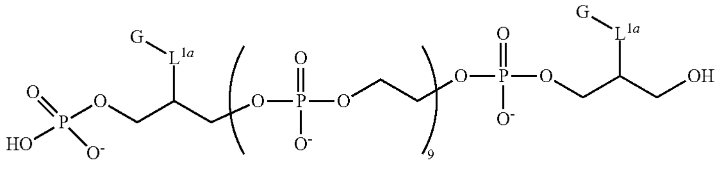 |

TABLE 3-continued
| Exemplary Compounds of Structure (II) | |
|---|---|
| Name | Structure |
| II-8 | 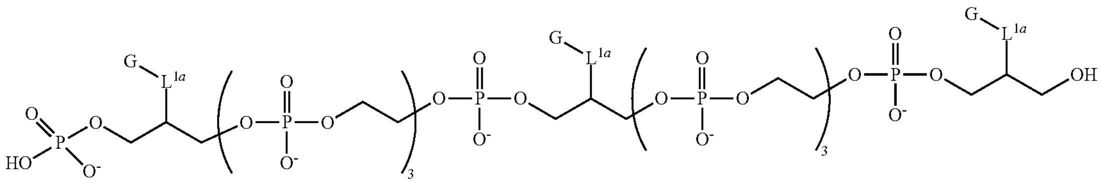 |
| II-9 | 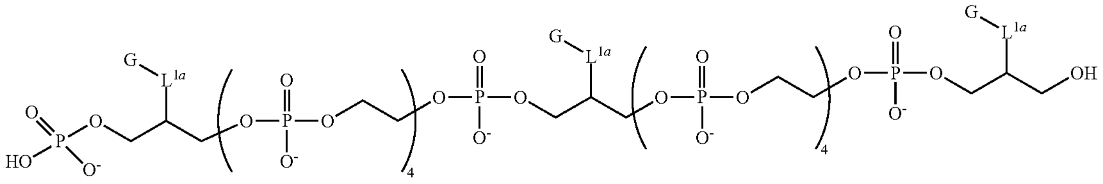 |
| II-10 | 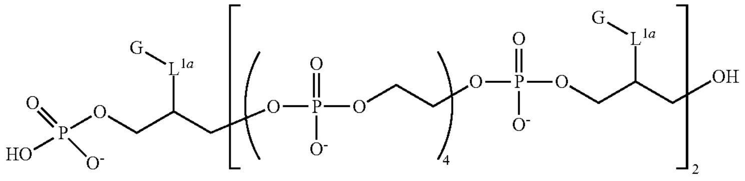 |
| II-11 | 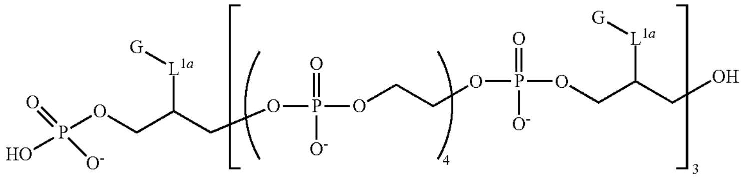 |
| II-12 | 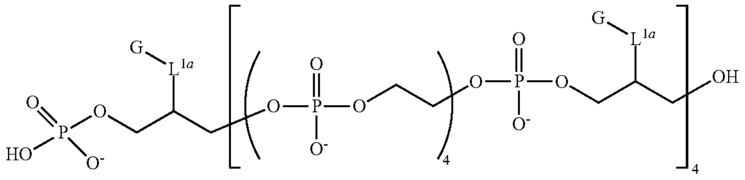 |
| II-13 | 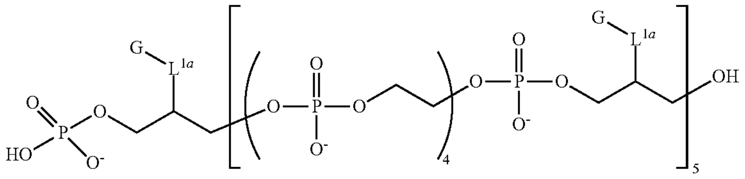 |
| II-14 | 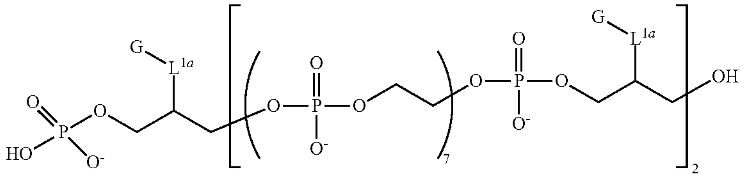 |
| II-15 | 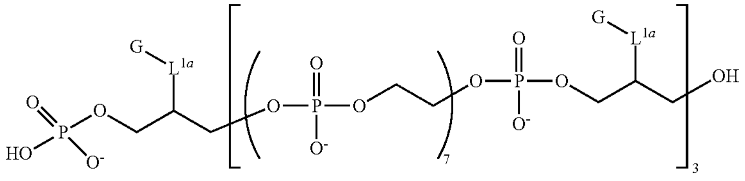 |

TABLE 3-continued

Exemplary Compounds of Structure (II)

| Name | Structure |
|---|---|
| II-16 | 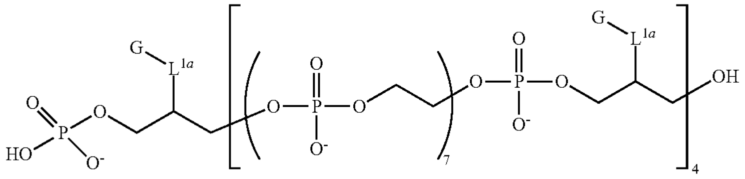 |
| II-17 | 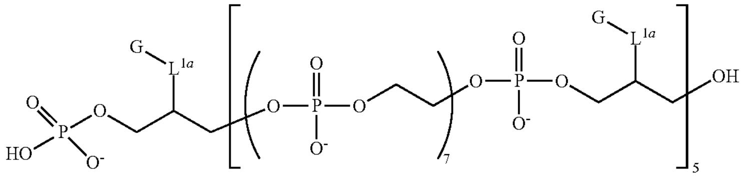 |
| II-18 | 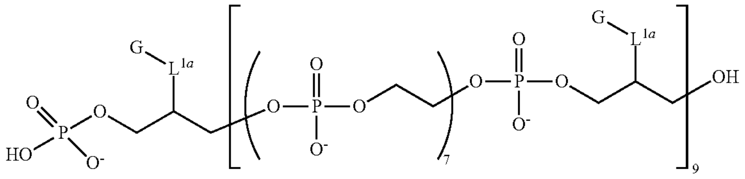 |
| II-19 | 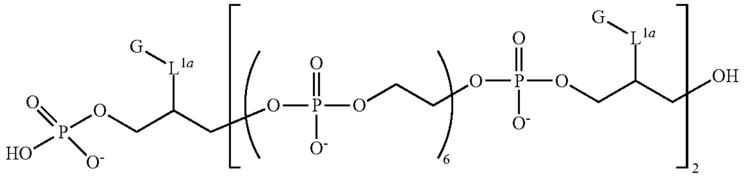 |
| II-20 | 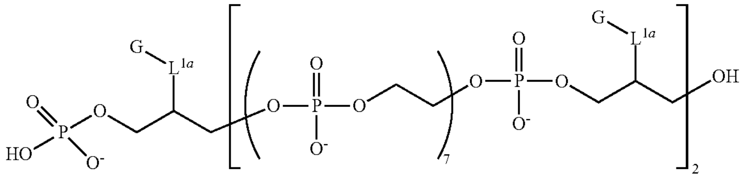 |
| II-21 | 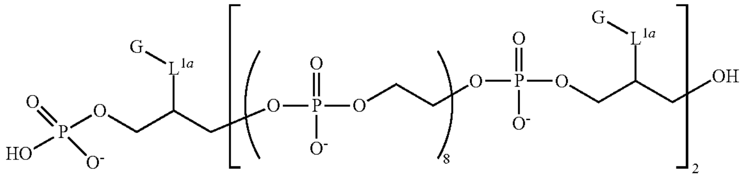 |
| II-22 | 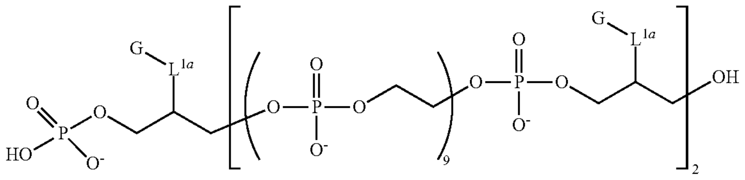 |

The compounds of structure (II) can be used in various methods, for example in embodiments is provided a method for labeling an analyte molecule, the method comprising:

(a) admixing any of the described compounds of structure (I), wherein $R^2$ or $R^3$ is Q or a linker comprising a covalent bond to Q, with the analyte molecule;

(b) forming a conjugate of the compound and the analyte molecule; and (c) reacting the conjugate with a compound of formula M-$L^{1b}$-G', thereby forming at least one covalent bond by reaction of at least one G and at least one G', wherein:

M is a moiety comprising two or more carbon-carbon double bonds and at least one degree of conjugation;

$L^{1b}$ is an optional alkylene, heteroalkylene or heteroatomic linker; and

G' is a reactive group complementary to G.

A different embodiment is a method for labeling an analyte molecule, the method comprising:

(a) admixing any of the compounds of structure (II) disclosed herein, wherein $R^2$ or $R^3$ is Q or a linker comprising a covalent bond to Q, with a compound of formula M-$L^{1b}$-G', thereby forming at least one covalent bond by reaction of G and G'; and (b) reacting the product of step (A) with the analyte molecule, thereby forming a conjugate of the product of step (A) and the analyte molecule, wherein:

M is a moiety comprising two or more carbon-carbon double bonds and at least one degree of conjugation;

$L^{1b}$ is an optional alkylene, heteroalkylene or heteroatomic linker; and

G' is a reactive group complementary to G.

Further, as noted above, the compound of structure (II) are useful for preparation of compounds of structure (I). Accordingly, in one embodiment is provided a method for preparing a compound of structure (I), the method comprising admixing a compound of structure (II) with a compound of formula M-$L^{1b}$-G', thereby forming at least one covalent bond by reaction of G and G', wherein:

M is a moiety comprising two or more carbon-carbon double bonds and at least one degree of conjugation;

$L^{1b}$ is an optional alkylene, heteroalkylene or heteroatomic linker; and

G' is a reactive group complementary to G.

The following examples are provided for purposes of illustration, not limitation.

EXAMPLES

General Methods $^1$H NMR spectra were obtained on a JEOL 400 MHz spectrometer. $^1$H spectra were referenced against TMS. Reverse phase HPLC analysis was performed using a Waters Acquity UHPLC system with a 2.1 mm×50 mm Acquity BEH-C18 column held at 45° C. Mass spectral analysis was performed on a Waters/Micromass Quattro micro MS/MS system (in MS only mode) using MassLynx 4.1 acquisition software. Mobile phase used for LC/MS was 100 mM 1,1,1,3,3,3-hexafluoro-2-propanol (HFIP), 8.6 mM triethylamine (TEA), pH 8. Phosphoramidites and precursor molecules were also analyzed using a Waters Acquity UHPLC system with a 2.1 mm×50 mm Acquity BEH-C18 column held at 45° C., employing an acetonitrile/water mobile phase gradient. Molecular weights for monomer intermediates were obtained using tropylium cation infusion enhanced ionization on a Waters/Micromass Quattro micro MS/MS system (in MS only mode). Size Exclusion chromatography (SEC) was accomplished with a Superdex 200 increase 5/150 GL analytical column. Isocratic elution with PBS buffer and a flow rate of 0.25 mL/min with a total run time of 17.5 min. Detection at 494, 405, 280 and 260 nm. Fractions of products were collected manually, pooled over successive runs. Lyophilized and reconstituted in 100 μL of water. Absorbance measurements were conducted on a Thermo Scientific Nanodrop 2000 spectrophotometer. Fluorescence measurements were conducted on a Thermo Scientific Nanodrop 3300 Fluorospectrometer.

All reactions were carried out in oven dried glassware under a nitrogen atmosphere unless otherwise stated. Commercially available DNA synthesis reagents were purchased from Glen Research (Sterling, VA). Anhydrous pyridine, toluene, dichloromethane, diisopropylethyl amine, triethylamine, acetic acid, pyridine, and THF were purchased from Aldrich. All other chemicals were purchase from Aldrich or TCI and were used as is with no additional purification.

Solid-Phase Synthesis

All compounds of structure (I) were synthesized on an ABI 394 DNA synthesizer using standard protocols for the phosphoramidite based coupling approach. The chain assembly cycle for the synthesis of oligonucleotide phosphoramidates was the following: (i) detritylation, 3% trichloroacetic acid in dichloromethane, 1 min; (ii) coupling, 0.1 M phosphoramidite and 0.45 M tetrazole in acetonitrile, 10 min; (iii) capping, 0.5 M acetic anhydride in THF/lutidine, 1/1, v/v 15 s; (iv) oxidation, 0.1 M iodine in THF/pyridine/water, 10/10/1, v/v/v, 30 s.

Chemical steps within the cycle were followed by acetonitrile washing and flushing with dry argon for 0.2-0.4 min. Cleavage from the support and removal of base and phosphoramidate protecting groups was achieved by treatment with ammonia for 1 hour at room temperature. Compounds were then analyzed by reverse phase HPLC as described above.

Compounds were synthesized on an Applied Biosystems 394 DNA/RNA synthesizer or on GE AKTÄ 10 OligoPilot on either 1 μmol or 10 μmol scales and possessed a 3'-phosphate group. Compounds were synthesized directly on CPG beads or on polystyrene solid support. The compounds were synthesized in the 3' to 5' direction by standard solid phase DNA methods. Coupling methods employed standard β-cyanoethyl phosphoramidite chemistry conditions. All phosphoramidite monomers were dissolved in acetonitrile/dichloromethane (0.1 M solutions), and were added in successive order using the following synthesis cycles: 1) removal of the 5'-dimethoxytrityl protecting group with dichloroacetic acid in toluene, 2) coupling of the next phosphoramidite with activator reagent in acetonitrile, 3) oxidation with iodine/pyridine/water, and 4) capping with acetic anhydride/1-methylimidizole/acetonitrile. Extendable alkyne (compound 9 or Glen Research 10-1992) phosphoramidite (100 mg) was dissolved in dry acetonitrile (700 uL) and dichloromethane (300 uL). A few sieves were added to the flask and it was blanketed with argon. The sequencer was utilized as described above. The synthesis cycle was repeated until the 5' Oligofloroside was assembled. At the end of the chain assembly, the monomethoxytrityl (MMT) group or dimthoxytrityl (DMT) group was removed with dichloroacetic acid in dichloromethane or dichloroacetic acid in toluene. The compounds were cleaved from the solid support using concentrated aqueous ammonium hydroxide at room temperature for 2-4 hours. The product was concentrated in vacuo and Sephadex G-25 columns were used to isolate the main product. Analysis was done with a RP-HPLC method couple to a mass spectrometer for molecular weight determination.

Example 1
Preparation of a Fluorescein (Fam) Azide Compound
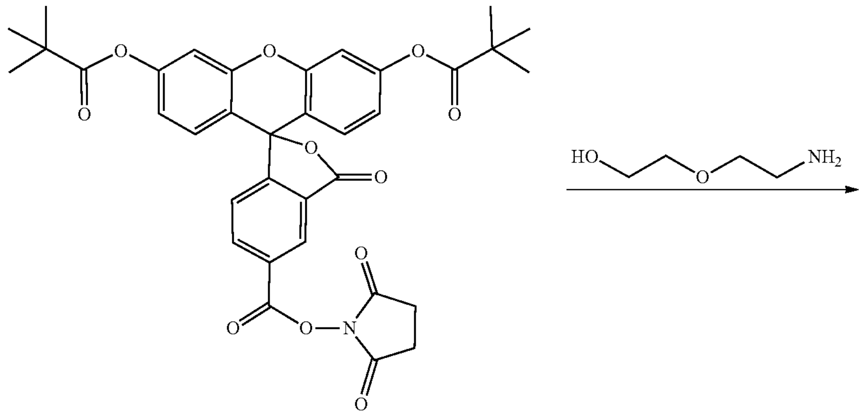
2
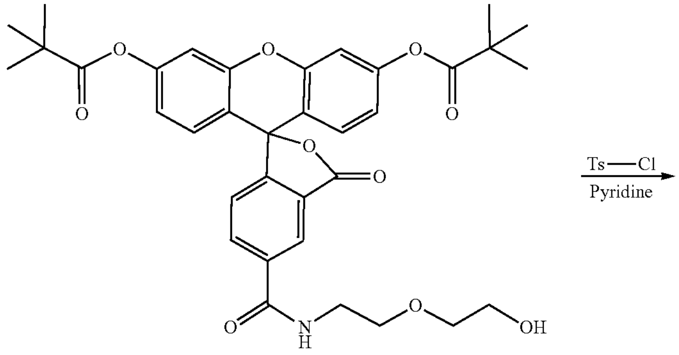
3
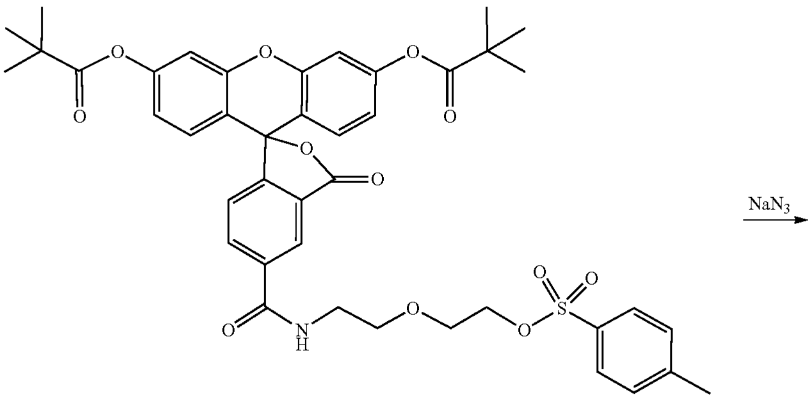
4

-continued

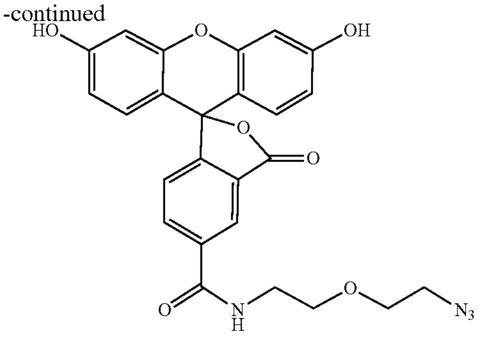

5

In a 250 ml round bottomed flask with magnetic stir bar and addition funnel was placed FAM-NHS ester 2 (2.24 g). Dichloromethane (35 mL) was added to the flask, stirring was initiated, flask placed under nitrogen and cooled on ice. In a separate beaker, 2-(2-aminoethoxy)ethanol (420 μL) was dissolved in dichloromethane (35 mL), methanol (7 mL) and triethylamine (1.5 mL) and the resulting solution was charged to the addition funnel. The amine solution was added dropwise to the NHS ester over 30 minutes. The final solution was stirred for 1 h at 0 C, the flask was removed from the ice bath and stirred at room temperature for 2 h. The reaction mixture was concentrated and the crude product was purified by silica gel chromatography. Product fractions were examined by TLC and LC/MS and pooled to afford 1.6 g (72%).

In a 250 mL round bottomed flask with magnetic stir bar was placed the FAM alcohol 3 (1.5 g) and chloroform (25 mL). To this solution was added pyridine (470 μL) and p-toluenesulfonyl chloride (691 mg). The mixture was stirred for 24 h at which point TLC indicated the reaction was incomplete, additional p-toluenesulfonyl chloride (1.4 g) and pyridine (1.5 mL) was added and the mixture stirred for an additional 24 h. TLC of the reaction after 48 h indicated the reaction was complete. The mixture was poured onto saturated sodium bicarbonate (200 mL) and dichloromethane (100 mL) in an extraction funnel and partitioned. The organic layer was retained and aqueous layer was extracted with dichloromethane (100 mL) two additional times. The organic layers were pooled and dried with sodium sulfate, filtered and concentrated. The crude product was purified by silica gel chromatography. Product fractions were identified by TLC and pooled to afford the desired tosylate 4 (1.8 g).

In a 200 mL round bottomed flask with magnetic stirrer was placed FAM-tosylate 4 (1.8 g) and DMF (15 mL) was added and the mixture was stirred to effect dissolution. To this was added sodium azide (830 mg) and the mixture heated to 50 C and stirred overnight. The mixture was poured onto 100 mM citric acid (150 mL) and ethyl acetate (150 mL) in an extraction funnel. The layers were partitioned and the organic layer retained. The aqueous layer was extracted with ethyl acetate two additional times. The organic layers were combined and dried over sodium sulfate. The solution was filtered and concentrated by rotary evaporation. The crude oil was purified by silica gel chromatography, product fractions were identified by TLC and pooled. The product was concentrated under vacuum to afford the desired FAM-aizde 5 as an orange solid (0.82 g). LCMS was consistent with the desired product.

Example 2

Synthesis of Alkyne Phosphoramidite

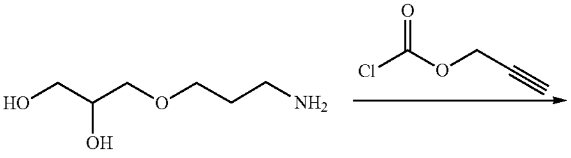

6

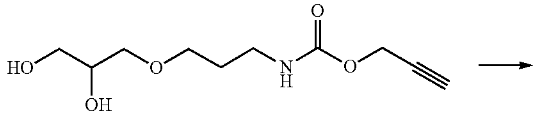

7

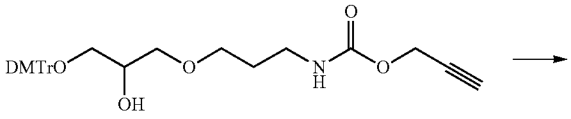

8

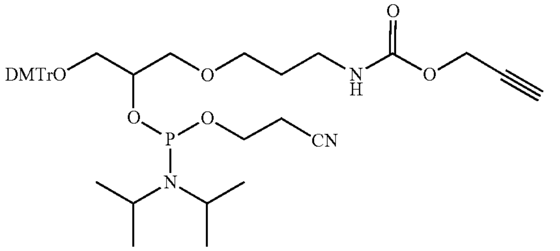

9

In a 500 mL round bottomed flask equipped with a addition funnel and magnetic stirrer was placed propargyl chloroformate (1.3 mL) in dichloromethane (75 mL). The flask was purged with nitrogen. In a separate beaker was placed aminoalcohol 6 (2.0 g) in dichloromethane (60 mL), methanol (10 mL) and triethylamine (1.4 mL). The addition funnel was charged with the aminoalcohol solution and was added dropwise over 30 minutes. The flask was stirred for 2 h at which point TLC indicated the reaction was complete. The reaction was concentrated on the rotary evaporator and further dried under high vacuum and used directly in the next step.

In a 500 mL round bottomed flask with magnetic stirrer was placed carbamate 7 (~3.1 g). Pyridine was added to the flask (270 mL) and stirring was initiated. Once the carbamate had been dissolved, the solution was placed on ice and stirred for 15 min under nitrogen. Dimethoxytrityl chloride (5.9 g) was added to the flask by powder funnel in a single portion. The flask was repurged with nitrogen and stirred at 0 C for 1 h. The flask was removed from ice and stirred at room temperature overnight. Methanol was added (10 mL) and the mixture stirred for 10 min. The mixture was concentrated on the rotovap and purified by silica gel chromatography. Product fraction were determined by TLC, pooled and concentrated to a final oil to afford mono-protected diol 8 (3.3 g).

In a 100 mL round bottomed flask with magnetic stir bar was placed monoprotected diol 8 (500 mg) and dichloromethane (5 mL). The mixture was stirred to the starting material was dissolved. Diisopropylethylamine (600 mg) and 2-cyanoethyl-N,N-diisopropylchlorophosphoramidite (440 mg) were added dropwise, simultaneously in separate syringes. The mixture was stirred for at which point TLC indicated the reaction was complete. The material was poured onto sodium bicarbonate solution, extracted with dichloromethane. The organic layer was dried with sodium sulfate, filtered and concentrated to an oil. Additional purification was accomplished by silica gel chromatography, Dichloromethane with 5% triethylamine. Product fractions were identified by TLC, pooled and concentrated. The final product was isolated as a clear oil (670 mg).

Example 3

Preparation and Characterization of Oligomer Dyes

3-, 5- and 10-mer polyalkyne oligomers were prepared from the phosphoramidite of Example 2. A representative 3-mer dye was prepared as follows:

In a 500 uL microcentrifuge tube was placed a solution of phosphate buffer (31.5 μL, 150 mM, pH=7.4). To this was added a solution of coumarin azide (22.5 μL, 10 mM in DMSO) and a solution of the polyalkyne (7.5 μL, 1 mM in water). In a separate 200 μL microcentrifuge tube was placed a solution of copper sulfate (3.0 μL, 50 mM), a solution of tris(3-hydroxypropyltriazolylmethyl)amine (THPTA, 3.0 μL, 100 mM) and a solution of sodium ascorbate (7.5 μL, 100 mM). The copper solution was mixed and the entire contents added to the coumarin azide/polyalkyne tube. The reaction was mixed and allowed to incubate overnight at room temperature. The mixture was diluted with water (75 μL) and purified by size exclusion chromatography (Superdex 200 increase 5/150 GL, isocratic elution with PBS, 0.25 mL/min, detection at 405 nM and 260 nM).

3-, 5- and 10-mer dyes with either a coumarin or fluorescein moiety were prepared in an analogous manner.

Figure 2:
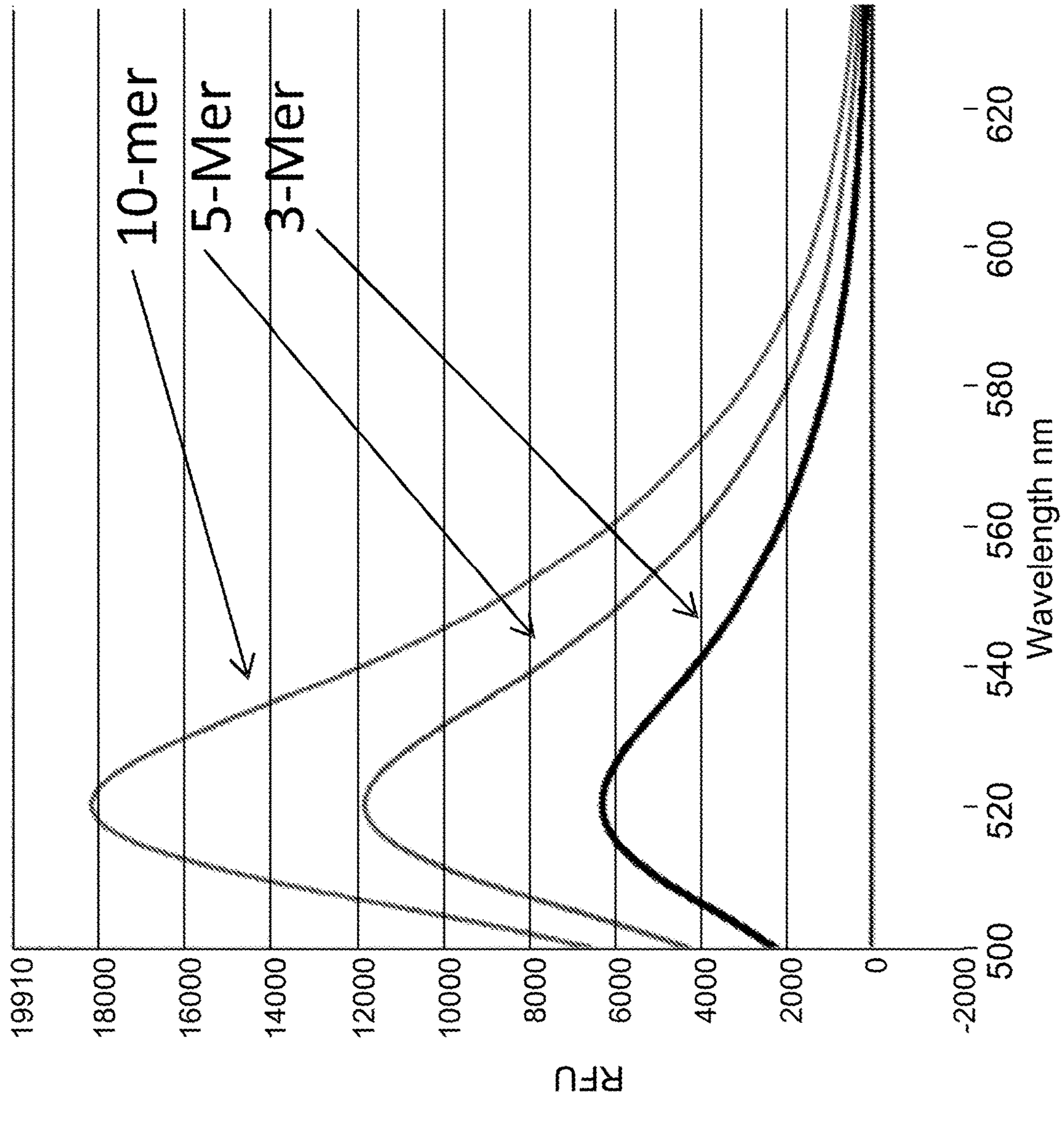
FIG. 2 provides fluorescence spectra for 3-mer, 5-mer and 10-mer fluorescein dye compounds.

The fluorescence spectra of coumarin and fluorescein-containing compounds were determined and are presented in FIGS. 1 and 2, respectively. The data show an increase in fluorescence with an increasing number of alkyne reactive sites, indicating that the azide is coupling with the alkyne to form a compound of structure (I).

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method, comprising:

labeling an analyte molecule, including:

(a) admixing an intermediary compound with a compound of formula M-$L^{1b}$-G', wherein the intermediary compound has the following structure (II), or a stereoisomer, salt or tautomer thereof:

(II)

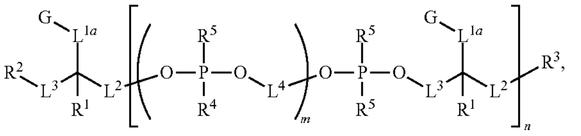

wherein:

$L^{1a}$, $L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently an alkylene, alkenylene, alkynylene, heteroalkylene, heteroalkenylene or heteroalkynylene linker;

$R^1$ is, at each occurrence, independently H, alkyl or alkoxy;

$R^2$ and $R^3$ are each independently H, OH, SH, alkyl, alkoxy, alkylether, —OP(=$R_a$)($R_b$)$R_c$, Q, a linker comprising a covalent bond to Q, a linker comprising a covalent bond to a solid support or a linker comprising a covalent bond to a further compound of structure (II), wherein: $R_a$ is O or S; $R_b$ is OH, SH, $O^-$, $S^-$, $OR_d$ or $SR_d$; $R_c$ is OH, SH, $O^-$, $S^-$, $OR_d$, $SR_d$, alkyl, alkoxy, alkylether, alkoxyalkylether, phosphate, thiophosphate, phosphoalkyl, thiophosphoalkyl, phosphoalkylether or thiophosphoalkylether; and $R_d$ is a counter ion, and wherein at least $R^2$ or $R^3$ is Q or a linker comprising a covalent bond to Q;

$R^4$ is, at each occurrence, independently OH, SH, $O^-$, $S^-$, $OR_d$ or $SR_d$;

$R^5$ is, at each occurrence, independently oxo, thioxo or absent;

Q is, at each occurrence, independently a moiety comprising a sulfhydryl, disulfide, activated ester, isothiocyanate, azide, alkyne, alkene, diene, dienophile, acid halide, sulfonyl halide, phosphine, α-haloamide, biotin, amino or maleimide functional group, wherein the activated ester is an N-succinimide ester, imidoester or polyflourophenyl ester;

m is, at each occurrence, independently an integer of zero or greater, wherein at least one occurrence of m is an integer of one or greater; and n is an integer of one or greater, and wherein admixing includes forming at least one covalent bond by reaction of G and G'; and (b) reacting the product of step (a) with the analyte molecule, including forming a conjugate of the product of step (a) and the analyte molecule, the analyte molecule being covalently attached to an end of the product of step (a);

wherein:

G is a moiety including an aldehyde, oxime, hydrazone, alkyne, amine, azide, acylazide, acylhalide, nitrile, nitrone, sulfhydryl, disulfide, sulfonyl halide, isothiocyanate, activated ester, ketone, α, β-unsaturated carbonyl, alkene, maleimide, α-haloimide, epoxide, aziridine, tetrazine, tetrazole, phosphine, biotin, or thiirane functional group, wherein the activated ester is an N-succinimide ester, imidoester or polyflourophenyl ester;

M is, at each occurrence, independently a moiety comprising two or more carbon-carbon double bonds and at least one degree of conjugation and at least one occurrence of M is a moiety comprising a carbocyclic or a heterocyclic;

$L^{1b}$ is an optional alkylene or heteroalkylene linker; and

G' is a reactive group complementary to G.

2. The method of claim 1, wherein M, at each occurrence, independently has one of the following structures:

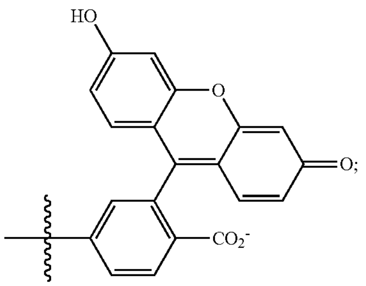

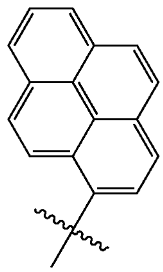

;

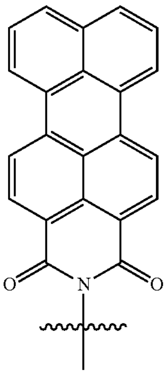

;

-continued

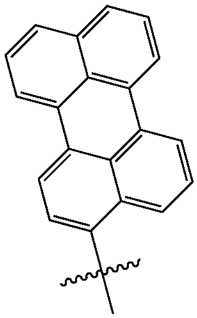

;

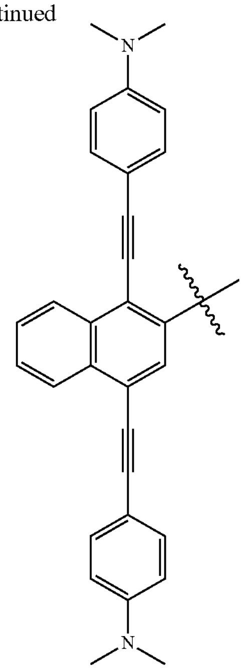

;

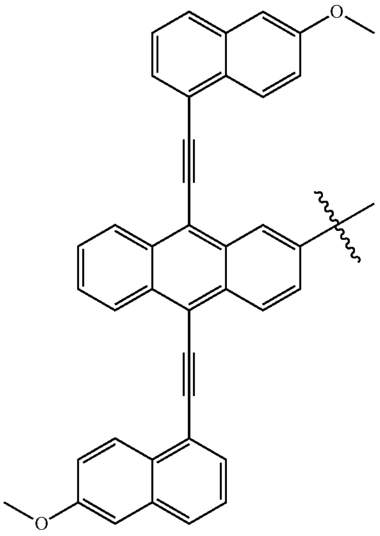

or

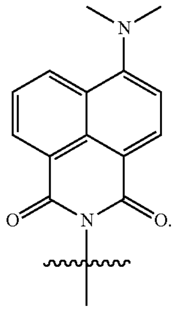 [SMILES: *N1C(=O)c2cccc3c(N(C)C)ccc(c23)C1=O]

3. The method of claim 1, wherein G is, at each occurrence, independently

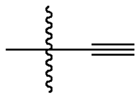

or

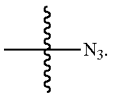

4. The method of claim 1, wherein M includes three or more rings selected from aryl and heteroaryl rings.

5. The method of claim 1, wherein n is an integer from 1 to 100.

6. The method of claim 1, wherein the analyte molecule is a nucleic acid, amino acid, a polymer, an enzyme, receptor, receptor ligand, antibody, glycoprotein, aptamer or prion.

7. The method of claim 1, wherein the conjugate has the following structure (I), or a stereoisomer, salt or tautomer thereof:

(I)

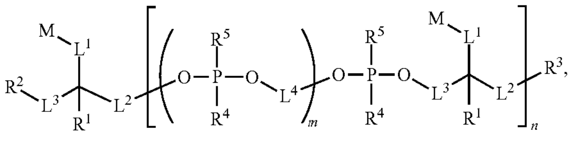

wherein:

M is, at each occurrence, independently a moiety comprising two or more carbon-carbon double bonds and at least one degree of conjugation and at least one occurrence of M is a moiety comprising a carbocyclic or a heterocyclic;

$L^1$ is, at each occurrence, independently a linker comprising an alkene, ester, amide, thioester, disulfide, carbocyclic, heterocyclic or heteroaryl group;

$L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently an alkylene, alkenylene, alkynylene, heteroalkylene, heteroalkenylene or heteroalkynylene linker;

$R^1$ is, at each occurrence, independently H, alkyl or alkoxy;

$R^2$ and $R^3$ are each independently H, OH, SH, alkyl, alkoxy, alkylether, —$OP(=R_a)(R_b)R_c$, a linker comprising a covalent bond to a solid support, a linker comprising a covalent bond to a further compound of structure (II), a linker covalently bonded to the analyte, or covalently bonded to the analyte, wherein: $R_a$ is O or S; $R_b$ is OH, SH, $O^-$, $S^-$, $OR_d$ or $SR_d$; $R_c$ is OH, SH, $O^-$, $S^-$, $OR_d$, $SR_d$, alkyl, alkoxy, alkylether, alkoxyalkylether, phosphate, thiophosphate, phosphoalkyl, thiophosphoalkyl, phosphoalkylether or thiophosphoalkylether; and $R_d$ is a counter ion, and wherein at least $R^2$ or $R^3$ is covalently bonded to the analyte or is a linker covalently bond to the analyte;

$R^4$ is, at each occurrence, independently OH, SH, $O^-$, $S^-$, $OR_d$ or $SR_d$;

$R^5$ is, at each occurrence, independently oxo, thioxo or absent;

Q is, at each occurrence, independently a moiety comprising a sulfhydryl, disulfide, activated ester, isothiocyanate, azide, alkyne, alkene, diene, dienophile, acid halide, sulfonyl halide, phosphine, «-haloamide, biotin, amino or maleimide functional group;

m is, at each occurrence, independently an integer of zero or greater, wherein at least one occurrence of m is an integer of one or greater; and n is an integer of one or greater.

8. The method of claim 7, wherein $L^1$ is formed by reaction of an alkyne and azide.

* * * * *